United States Patent
Kozak et al.

(10) Patent No.: US 11,420,965 B2
(45) Date of Patent: *Aug. 23, 2022

(54) PYRIMIDINE COMPOUND AS JAK KINASE INHIBITOR

(71) Applicant: THERAVANCE BIOPHARMA R&D IP, LLC, South San Francisco, CA (US)

(72) Inventors: Jennifer Kozak, Pacifica, CA (US); Ryan Hudson, San Mateo, CA (US); Gary E. L. Brandt, Alameda, CA (US); Robert Murray McKinnell, Millbrae, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/301,243

(22) Filed: Mar. 30, 2021

(65) Prior Publication Data

US 2021/0214349 A1 Jul. 15, 2021

Related U.S. Application Data

(63) Continuation of application No. 16/991,268, filed on Aug. 12, 2020, now Pat. No. 10,988,470, which is a continuation of application No. 16/737,067, filed on Jan. 8, 2020, now Pat. No. 10,774,080, which is a continuation of application No. 16/390,175, filed on Apr. 22, 2019, now Pat. No. 10,562,894, which is a continuation of application No. 16/171,693, filed on Oct. 26, 2018, now Pat. No. 10,308,646.

(60) Provisional application No. 62/577,852, filed on Oct. 27, 2017.

(51) Int. Cl.
| | |
|---|---|
| *C07D 451/14* | (2006.01) |
| *A61K 45/06* | (2006.01) |
| *C07D 451/04* | (2006.01) |
| *A61P 17/14* | (2006.01) |
| *A61P 37/06* | (2006.01) |
| *A61P 17/00* | (2006.01) |
| *A61K 9/00* | (2006.01) |
| *A61K 9/06* | (2006.01) |
| *A61K 31/506* | (2006.01) |
| *C07D 403/12* | (2006.01) |

(52) U.S. Cl.
CPC ......... *C07D 451/14* (2013.01); *A61K 9/0014* (2013.01); *A61K 9/06* (2013.01); *A61K 31/506* (2013.01); *A61K 45/06* (2013.01); *A61P 17/00* (2018.01); *A61P 17/14* (2018.01); *A61P 37/06* (2018.01); *C07D 403/12* (2013.01); *C07D 451/04* (2013.01); *C07B 2200/13* (2013.01)

(58) Field of Classification Search
CPC .. C07D 451/14; C07D 403/12; C07D 451/04; A61P 17/14; A61P 37/06; A61P 17/00; A61K 9/0014; A61K 9/06; A61K 31/506; A61K 45/06; C07B 2200/13
USPC .......................................................... 514/275
See application file for complete search history.

(56) References Cited

U.S. PATENT DOCUMENTS

| | | | |
|---|---|---|---|
| 6,653,300 | B2 | 11/2003 | Bebbington et al. |
| 6,660,731 | B2 | 12/2003 | Bebbington et al. |
| 6,664,247 | B2 | 12/2003 | Bebbington et al. |
| 7,531,536 | B2 | 5/2009 | Bebbington et al. |
| 7,625,913 | B2 | 12/2009 | Bebbington et al. |

(Continued)

FOREIGN PATENT DOCUMENTS

| | | |
|---|---|---|
| WO | 2007/059299 A1 | 5/2007 |
| WO | 2008/005538 A2 | 1/2008 |

(Continued)

OTHER PUBLICATIONS

Abcouwer, "Angiogenic factors and cytokines in diabetic retinopathy", J Clin Cell Immunol, Supplement 1: 1-12 (2013).

(Continued)

*Primary Examiner* — Kristin A Vajda
(74) *Attorney, Agent, or Firm* — Jeffrey A. Hagenah; Sheppard Mullin Richter & Hampton LLP

(57) ABSTRACT

The invention provides a compound of formula (I):

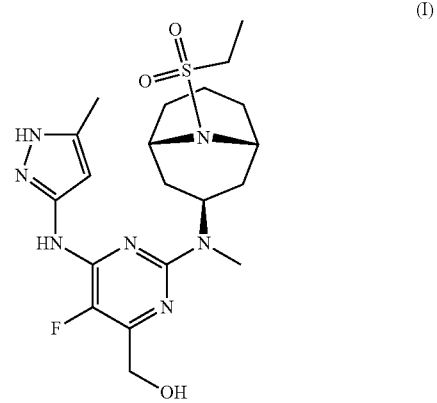

or a pharmaceutically-acceptable salt thereof, that is an inhibitor of JAK kinases. The invention also provides pharmaceutical compositions comprising such compound, a crystalline form, methods of using such compound to treat inflammatory skin diseases and other diseases, and processes and intermediates useful for preparing such compound.

18 Claims, 4 Drawing Sheets

(56) References Cited

U.S. PATENT DOCUMENTS

| | | |
|---|---|---|
| 7,691,853 B2 | 4/2010 | Bebbington et al. |
| 7,951,820 B2 | 5/2011 | Bebbington et al. |
| 8,222,256 B2 | 7/2012 | Zhang |
| 8,815,877 B2 | 8/2014 | Aliagas-Martin et al. |
| 9,725,470 B2 | 8/2017 | Hudson et al. |
| 10,028,960 B2 | 7/2018 | Hudson et al. |
| 10,308,646 B2 | 6/2019 | Kozak et al. |
| 10,485,803 B2 | 11/2019 | Huang |
| 10,562,894 B2 | 2/2020 | Kozak et al. |
| 10,774,080 B2 | 9/2020 | Kozak et al. |
| 10,988,470 B2 * | 4/2021 | Kozak ............ A61K 9/0014 |
| 2008/0004302 A1 | 1/2008 | Theoclitou et al. |
| 2009/0312543 A1 | 12/2009 | Bebbington et al. |
| 2016/0052930 A1 | 2/2016 | Fensome et al. |
| 2020/0046709 A1 | 2/2020 | Hudson et al. |
| 2020/0338073 A1 | 10/2020 | Gerken et al. |
| 2020/0339580 A1 | 10/2020 | Gerken et al. |
| 2020/0369660 A1 | 11/2020 | Kozak et al. |

FOREIGN PATENT DOCUMENTS

| | | |
|---|---|---|
| WO | 2013/092940 A1 | 6/2013 |
| WO | 2015/094803 A1 | 6/2015 |

OTHER PUBLICATIONS

Baliwag et al., "Cytokines in psoriasis", Cytokine, 73(2): 342-350 (Jun. 2015).

Bao et al., "The involvement of the JAK-STAT signaling pathway in chronic inflammatory skin disease atopic dermatitis", JAK-STAT, 2(3): e24137-1-e24137-8 (2013).

Coghill et al., "Effector CD4+ T cells, the cytokines they generate, and GVHD: something old and something new", Blood, 117(12): 3268-3276 (Mar. 24, 2011).

Craiglow et al., "Tofacitinib citrate for the treatment of vitiligo: A pathogenesis-directed therapy", JAMA Dermatology, 151: 1110-1112 (2015).

Danese, "New therapies for inflammatory bowel disease: from the bench to the bedside", Gut, 61: 918-932 (2012).

De Nitto et al., "Involvement of interleukin-15 and interleukin-21, two gamma-chain-related cytokines, in celiac disease", World J Gastroenterol, 15(37): 4609-4614 (Oct. 7, 2009).

Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).

Horai et al, "Cytokines in autoimmune uveitis", Journal of Interferon & Cytokine Research, 31(10): 733-744 (2011).

Ishizaki et al., "Involvement of tyrosine kinase-2 in both the IL-12/Th1 and IL-23/Th17 axes in vivo", J Immunol, 187: 181-189 (2011).

Knickelbein et al., "Inflammatory mechanisms of age-related macular degeneration", International Ophthalmology Clinics, 55(3): 63-78 (2015).

Kozak, "Discovery and profiling of novel, intestinally-restricted oral pan-JAK inhibitors for the treatment of inflammatory bowel diseases", (Apr. 2017).

Kozak, "Discovery and profiling of novel, intestinally-restricted oral pan-JAK inhibitors for the treatment of inflammatory bowel diseases", (Jun. 2017).

Kozak et al., "Discovery and profiling of novel, intestinally-restricted oral pan-JAK inhibitors for the treatment of inflammatory bowel diseases", Poster at the Gordon Research Conference (Aug. 6-11, 2017).

Kudlacz et al., "The JAK-3 inhibitor CP-690550 is a potent anti-inflammatory agent in a murine model of pulmonary eosinophilia", European Journal of Pharmacology, 582: 154-161 (2008).

Kumawat et al., "Microscopic colitis patients demonstrate a mixed Th17/Tc17 and Th1/Tc1 mucosal cytokine profile", Molecular Immunology, 55: 355-364 (2013).

Leung et al., "New insights into atopic dermatitis", J Clin Invest, 113(5): 651-657 (2004).

Malaviya et al., "Janus Kinase-3 dependent inflammatory responses in allergic asthma", International Immunopharmacology, 10: 829-836 (2010).

Matsunaga et al., "Effects of a Janus kinase inhibitor, pyridone 6, on airway responses in a murine model of asthma", Biochemical and Biophysical Research Communications, 404: 261-267 (2011).

Mozaffari et al., "New biologic therapeutics for ulcerative colitis and Crohn's disease", Expert Opin Biol Ther, 14(5): 583-600 (2014).

Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).

Okiyama et al., "Reversal of CD8 T-cell-mediated mucocutaneous graft-versus-host-like disease by the JAK inhibitor tofacitinib", Journal of Investigative Dermatology, 134: 992-1000 (2014).

Reimund et al., "Mucosal inflammatory cytokine production by intestinal biopsies in patients with ulcerative colitis and Crohn's disease", Journal of Clinical Immunology, 16(3): 144-150 (1996).

Schadler et al., "Biologies for the primary care physician: Review and treatment of psoriasis", Disease-a-month, 000: 1-40 (2018).

Shchuko et al., "Intraocular cytokines in retinal vein occlusion and its relation to the efficiency of anti-vascular endothelial growth factor therapy", Indian Journal of Ophthalmology, 63(12): 905-911 (2015).

Sohn et al., "Changes in aqueous concentrations of various cytokines after intravitreal triamcinolone versus bevacizumab for diabetic macular edema", Ophthalmology, 152: 686-694 (2011).

Sonkoly et al., "IL-31: A new link between T cells and pruritus in atopic skin inflammation", J Allergy Clin Immunol, 117(2): 411-417 (2006).

Stallmach et al., "Cytokine/chemokine transcript profiles reflect mucosal inflammation in Crohn's disease", Int J Colorectal Dis, 19: 308-315 (2004).

Stevenson et al., "Dry eye disease", Arch Ophthalmol, 130(1): 90-100 (Jan. 2012).

Tanaka et al., "New insight into mechanisms of pruritus from molecular studies on familial primary localized cutaneous amyloidosis", British Journal of Dermatology, 161: 1217-1224 (2009).

Weinbrand-Goichberg et al., "Eosinophilic esophagitis: an immune-mediated esophageal disease", Immunol Res, 56: 249-260 (2013).

Welz-Kubiak et al., "IL-31 is overexpressed in lichen planus but its level does not correlate with pruritus severity", Journal of Immunology Research, Article 854747, 6 pages (2015).

Woywodt et al., "Mucosal cytokine expression, cellular markers and adhesion molecules in inflammatory bowel disease", European Journal of Gastroenterology & Hepatology, 11: 267-276 (1999).

King et al., "Alopecia areata is driven by cytotoxic T lymphocytes and is reversed by JAK inhibition", Nature Medicine, 20(9): 1043-1049 (Sep. 2014).

Yamamoto et al., "Mucosal inflammation in the terminal ileum of ulcerative colitis patients: Endoscopic findings and cytokine profiles", Digestive and Liver Disease, 40: 253-259 (2008).

Yano et al., "Ipilimumab augments antitumor activity of bispecific antibody-armed T cells", Journal of Translational Medicine, 12: 191 (2014).

Zhou et al., "Cytokines and Behcet's Disease", Autoimmunity Reviews, 11: 699-704 (2012).

The International Search Report and the Written Opinion for PCT application No. PCT/US2018/057682 dated Jan. 16, 2019.

Kozak et al., U.S. Appl. No. 16/171,693, filed Oct. 26, 2018.

Kozak et al., U.S. Appl. No. 16/390,175, filed Apr. 22, 2019.

Kozak et al., U.S. Appl. No. 16/737,067, filed Jan. 8, 2020.

Kozak et al., U.S. Appl. No. 16/991,268, filed Aug. 12, 2020.

* cited by examiner

PYRIMIDINE COMPOUND AS JAK KINASE INHIBITOR

CROSS-REFERENCE TO RELATED APPLICATIONS

This application is a continuation application of U.S. Ser. No. 16/991,268 filed on Aug. 12, 2020, now U.S. Pat. No. 10,988,470, which is a continuation application of U.S. Ser. No. 16/737,067, filed on Jan. 8, 2020, now U.S. Pat. No. 10,774,080, which is a continuation application of U.S. Ser. No. 16/390,175, filed on Apr. 22, 2019, now U.S. Pat. No. 10,562,894, which is a continuation application of U.S. Ser. No. 16/171,693, filed on Oct. 26, 2018, now U.S. Pat. No. 10,308,646, which application claims the benefit of U.S. Provisional Application No. 62/577,852, filed on Oct. 27, 2017; the disclosures of which are incorporated herein by reference in their entirety.

BACKGROUND OF THE INVENTION

Field of the Invention

The invention is directed to a pyrimidine compound useful as a JAK kinase inhibitor. The invention is also directed to pharmaceutical compositions comprising such compound, crystalline forms of such compounds, methods of using such compound to treat inflammatory and autoimmune diseases, and processes and intermediates useful for preparing such compound.

State of the Art

Inhibition of the family of JAK enzymes can inhibit signaling of many key pro-inflammatory cytokines. Thus JAK inhibitors are likely to be useful in the treatment of atopic dermatitis and other inflammatory skin diseases, allergic rhinitis, asthma, chronic obstructive pulmonary disease (COPD) and other pulmonary inflammatory diseases, ulcerative colitis and other gastrointestinal inflammatory, as well as ocular inflammatory diseases.

Atopic dermatitis (AD) is a common chronic inflammatory skin disease that affects an estimated 14 million people in the United States alone. It is estimated that AD affects 10 to 20% of children and 1 to 3% of adults in developed countries (Bao et al., *JAK-STAT*, 2013, 2, e24137) and the prevalence is increasing. Elevation of proinflammatory cytokines that rely on the JAK-STAT pathway, in particular, IL-4, IL-5, IL-10, IL-12, IL-13, IFNγ, and TSLP has been associated with AD (Bao et al., Leung et al., *The Journal of Clinical Investigation*, 2004, 113, 651-657). In addition, upregulation of IL-31, another cytokine that signals through a JAK pairing, has been shown to have a role in the pruritus associated with the chronic state of AD (Sonkoly et al., *Journal of Allergy and Clinical Immunology*, 2006, 117, 411-417).

Due to the modulating effect of the JAK/STAT pathway on the immune system, systemic exposure to JAK inhibitors may have an adverse systemic immunosuppressive effect. Therefore, it would be desirable to provide a new JAK inhibitor which has its effect at the site of action without significant systemic effects. In particular, for the treatment of inflammatory skin diseases, such as atopic dermatitis, it would be desirable to provide a new JAK inhibitor which can be administered topically and achieve therapeutically relevant exposure in the skin which is rapidly cleared to minimize systemic exposure.

SUMMARY OF THE INVENTION

In one aspect, the invention provides a compound having activity as a JAK kinase inhibitor.

Accordingly, the invention provides a compound of formula (I):

(I)

or a pharmaceutically-acceptable salt thereof.

The invention also provides a crystalline form of compound (I).

The invention also provides a pharmaceutical composition comprising compound (I) and a pharmaceutically-acceptable carrier.

The invention also provides a method of treating inflammatory and autoimmune diseases of the skin, in particular atopic dermatitis and alopecia areata, in a mammal, the method comprising administering compound (I), or a pharmaceutically acceptable salt thereof, to the mammal.

The invention also provides synthetic processes and intermediates described herein, which are useful for preparing compound (I).

The invention also provides compound (I) as described herein for use in treating inflammatory diseases or disorders.

BRIEF DESCRIPTION OF THE DRAWINGS

Various aspects of the present invention are illustrated by reference to the accompanying drawings.

DETAILED DESCRIPTION OF THE INVENTION

Figure 1:
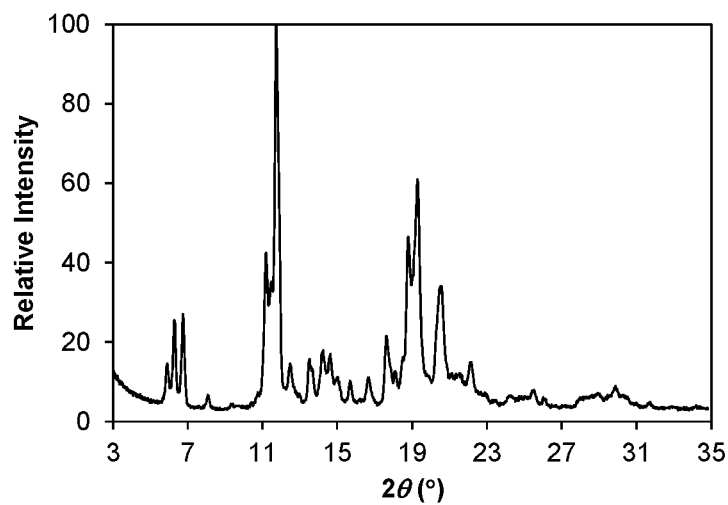
FIG. 1 shows a powder x-ray diffraction (PXRD) pattern of crystalline Form I of compound (I) (hereinafter Form I).

Among other aspects, the invention provides a JAK kinase inhibitor of formula (I), pharmaceutically-acceptable salts thereof, and intermediates for the preparation thereof.

Chemical structures are named herein according to IUPAC conventions as implemented in ChemDraw software (PerkinElmer, Inc., Cambridge, Mass.). For example, compound (I):

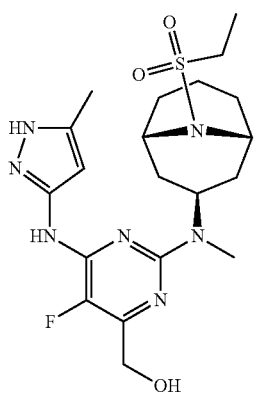

is designated as (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol.

The (1R,3s,5S) notation describes the exo orientation of the pyrimidinylamino group with respect to the 9-azabicyclo[3.3.1]nonane group.

Furthermore, the pyrazolyl moiety of compound (I) as well as other compounds disclosed herein exists in tautomeric form. It will be understood that although specific structures are shown, or named, in a particular form, the invention also includes the tautomer thereof.

The compounds of the disclosure contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compound (I) may exist as a free form or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled versions of the compounds of the disclosure, including compound (I), where an atom has been replaced or enriched with an atom having the same atomic number but an atomic mass different from the atomic mass that predominates in nature. Examples of isotopes that may be incorporated into a compound of formula (I) include, but are not limited to, $^{2}H$, $^{3}H$, $^{11}C$, $^{13}C$, $^{14}C$, $^{13}N$, $^{15}N$, $^{15}O$, $^{17}O$, $^{18}O$, $^{35}S$, and $^{18}F$. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "halogen" means fluoro, chloro, bromo or iodo.

The term "heterocyclyl", "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), triisopropylsilyl (TIPS), tert-butyldimethylsilyl (TBS or TBDMS), [2-(trimethylsilyl)-ethoxy]methyl (SEM); and the like. Numerous protecting groups, and their introduction and removal, are described in T. W. Greene and P. G. M. Wuts, *Protecting Groups in Organic Synthesis*, Third Edition, Wiley, New York General Synthetic Procedures Compound (I), and intermediates thereof, can be prepared according to the following general methods and procedures using commercially-available or routinely-prepared starting materials and reagents. The substituents and variables (e.g., R, and X) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials known to those skilled in the art. In particular, it will be appreciated that compound (I) may be prepared by a variety of process routes in which reactants are combined in different orders to provide different intermediates en route to producing the final product.

General methods of preparing compound (I) are illustrated in schemes 1 and 2.

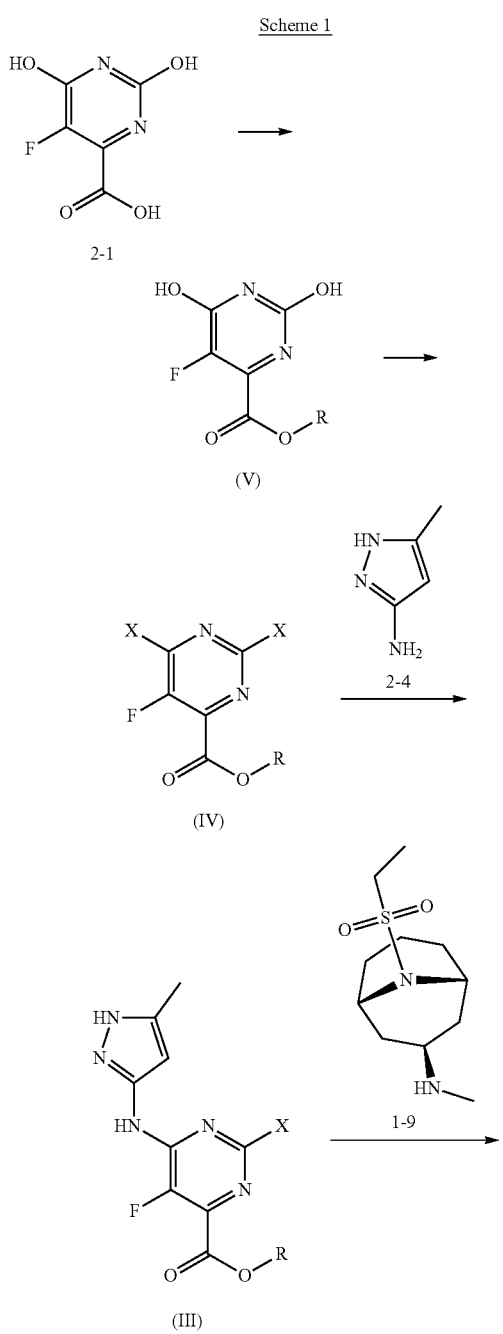

Scheme 1

Scheme 2

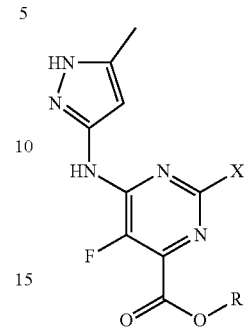
(III)

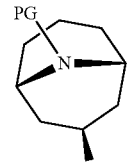
(VI)

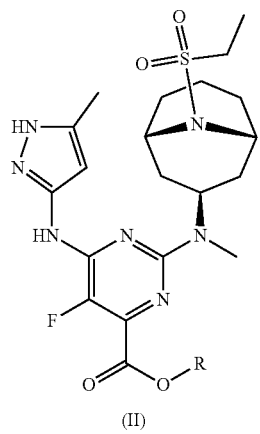
(II)

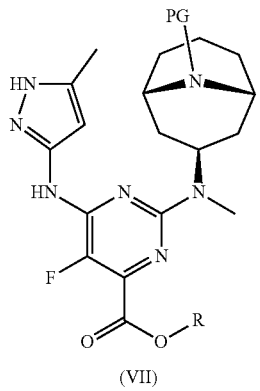
(VII)

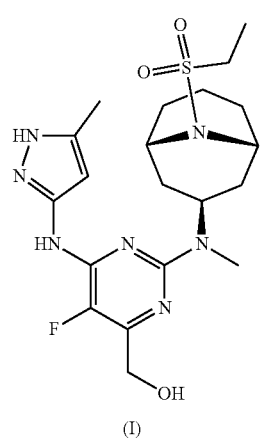
(I)

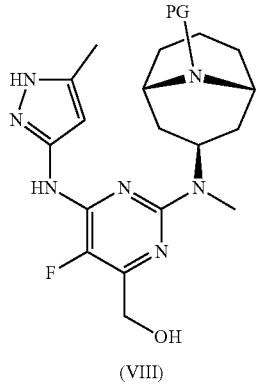
(VIII)

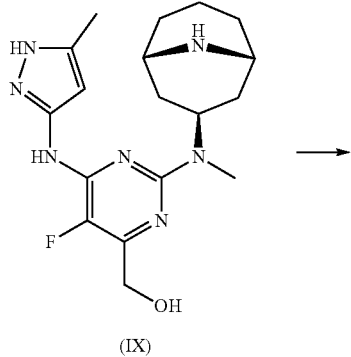
(IX)

Starting material 2-1 may be converted to ester (V), by reaction with an alcohol in presence of an acid, where R is an alkyl group. In some embodiments, R is a $C_{1-12}$ alkyl group. In some embodiments the alcohol is ethanol. Compound (V) may be converted to the di-halo compound (IV). In some embodiments, (IV) is a di-chloro analog. In some embodiments, the reagent is $POCl_3$. Compound (IV) may be converted to (III) by reaction with 2-4 in presence of a base. Compound (II) may be formed by reacting (III) with 1-9 in the presence of a base. Finally, (II) may be reduced to (I) in presence of a reducing agent. In some embodiments, the reducing agent is a lithium or sodium hydride source. In some embodiments, the reducing agent is $LiAlH_4$, $NaBH_4$, or $LiBH_4$. In some embodiments, R is ethyl. Optionally, a pharmaceutically acceptable salt of (I) may be formed.

For this general method, in some embodiments, R is a $C_{1-12}$ alkyl. In some embodiments, R is a $C_{1-6}$ alkyl. In some embodiments, R is a $C_{1-3}$ alkyl. In some embodiments, R is ethyl. In some embodiments, X is F, Cl or Br. In some embodiments, X is Cl. In some embodiments, R is ethyl and X is Cl.

-continued

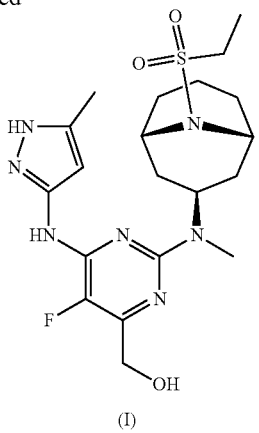

(I)

Alternatively, compound (III) may be reacted with compound (VI) wherein PG is an amino-protecting group, in presence of a base, such as DIPEA, to give compound (VII). Compound (VII) may be reduced to the corresponding alcohol (VIII) with a reducing agent. In some embodiments, the reducing agent is a lithium or sodium hydride source. In some embodiments, the reducing agent is LiAlH$_4$, NaBH$_4$, or LiBH$_4$. Compound (VIII) may be deprotected to give compound (IX). When PG is Boc, the deprotection may be conducted in presence of a strong acid such as TFA or HCl. Finally, compound (IX) may be reacted with a source of ethanesulfonyl such as ethanesulfonyl chloride.

For this general method, in some embodiments, PG is tert-butoxycarbonyl (Boc). In some embodiments, R is a $C_{1-12}$ alkyl. In some embodiments, R is a $C_{1-6}$ alkyl. In some embodiments, R is a $C_{1-3}$ alkyl. In some embodiments, R is ethyl. In some embodiments, X is F, Cl or Br. In some embodiments, X is Cl. In some embodiments, R is ethyl and X is Cl.

Crystalline Form I

In another aspect, the disclosure provides a crystalline form (Form I) of compound (I)

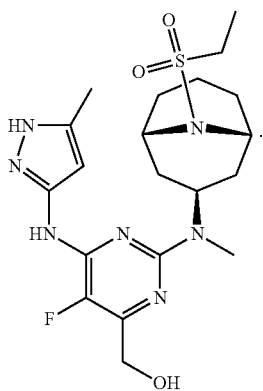

(I)

In one aspect, the crystalline form is characterized by a powder X-ray diffraction comprising diffraction peaks at 2θ values of 11.19±0.20, 11.73±0.20, 18.80±0.20, and 19.29±0.20. In another aspect, the crystalline form is further characterized by having an additional diffraction peaks at a 2θ value of 6.75±0.20. In another aspect, the crystalline form is further characterized by having two or more additional diffraction peaks at 2θ values selected from 5.91±0.20, 6.28±0.20, 8.08±0.20, 16.68±0.20, 17.62±0.20, 20.53±0.20, and 22.16±0.20.

As is well known in the field of powder X-ray diffraction, peak positions of PXRD patterns are relatively less sensitive to experimental details, such as details of sample preparation and instrument geometry, than are the relative peak heights. Thus, in one aspect, the crystalline Form I is characterized by a powder X-ray diffraction pattern in which the peak positions are substantially in accordance with the peak positions of the pattern shown in FIG. 1.

In another aspect, crystalline Form I is characterized by its behavior when exposed to high temperature. As demonstrated in FIG. 2, the differential scanning calorimetry (DSC) trace recorded at a heating rate of 10° C. per minute exhibits a peak in endothermic heat flow, identified as a melt transition, which shows a maximum in endothermic heat flow at a temperature of 250.9° C.±2° C. In another aspect form I is characterized by a differential scanning calorimetry trace substantially in accordance with that shown in FIG. 2.

Figure 3:
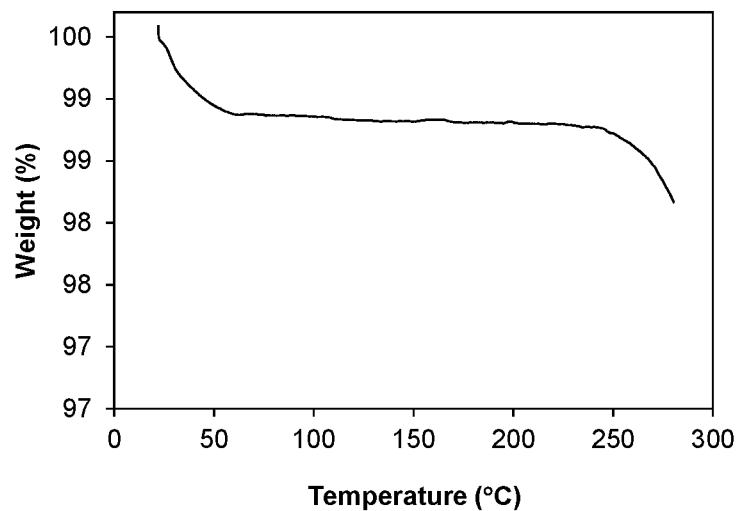
FIG. 3 shows a thermal gravimetric analysis (TGA) plot of crystalline Form I.

The thermal gravimetric analysis (TGA) trace of FIG. 3 exhibits a weight loss of about 0.70% between 22° C. and 125° C., under N$_2$ purge. The compound decomposes at an onset temperature of about 250° C.

As described in Preparation 2, Form I may be prepared by dissolving compound (I) in ethanol upon heating. The resulting solution is then cooled to about 25° C. Form I may be isolated by filtration.

In another aspect, the invention provides a method of preparing crystalline Form I, the method comprising: (a) dissolving compound (I) in a diluent such as ethanol and optionally applying heating to form a reaction mixture; (b) cooling the solution to about 25° C. with optional stirring; and (c) isolating crystalline Form I from the reaction mixture, for example by filtration.

Crystalline Form II

In another aspect, the invention provides a crystalline form (Form II) of compound (I):

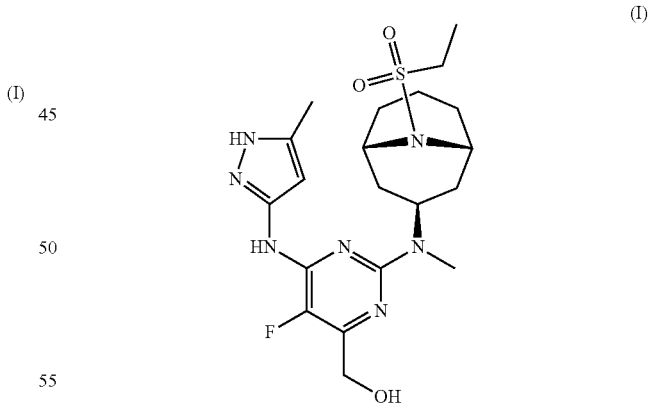

(I)

which is a freebase anhydrous crystalline form.

In one aspect, the crystalline form is characterized by a powder X-ray diffraction comprising diffraction peaks at 2θ values of 11.4±0.2, 16.2±0.2, 16.6±0.2, 17.7±0.2, and 21.9±0.2.

In another aspect, the crystalline form is further characterized by having additional diffraction peaks at 2θ values of 8.9±0.2, 9.5±0.2, and 10.2±0.2.

In another aspect, the crystalline form is further characterized by having two or more additional diffraction peaks at 2θ values selected from 14.4±0.2, 19.0±0.2, 19.2±0.2, 19.8±0.2, 20.1±0.2, 20.4±0.2, 20.6±0.2, 20.8±0.2, 21.3±0.2, 25.9±0.2, 30.1±0.2, 30.5±0.2, 30.9±0.2, 32.6±0.2, and 33.8±0.2.

As is well known in the field of powder X-ray diffraction, peak positions of PXRD patterns are relatively less sensitive to experimental details, such as details of sample preparation and instrument geometry, than are the relative peak heights. Thus, in one aspect, the crystalline Form II is characterized by a powder X-ray diffraction pattern in which the peak positions are substantially in accordance with the peak positions of the pattern shown in FIG. 5.

In another aspect, crystalline Form II is characterized by its behavior when exposed to high temperature. As demonstrated in FIG. 6, the differential scanning calorimetry (DSC) trace recorded at a heating rate of 10° C. per minute exhibits a peak in endothermic heat flow, identified as a melt transition, which shows a maximum in endothermic heat flow at a temperature of 238.1° C.±2° C. In another aspect form II is characterized by a differential scanning calorimetry trace substantially in accordance with that shown in FIG. 6.

Figure 7:
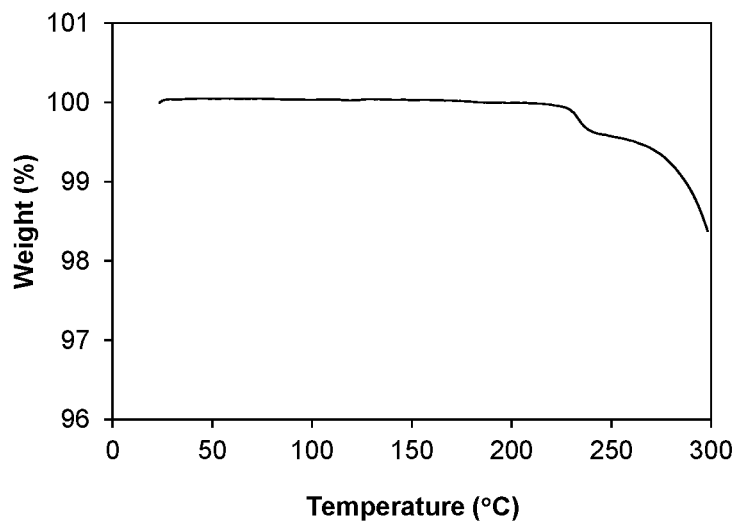
FIG. 7 shows a thermal gravimetric analysis (TGA) plot of crystalline Form II.

The thermal gravimetric analysis (TGA) trace of FIG. 7 exhibits a weight loss associated with decomposition after 222° C.

Figure 8:
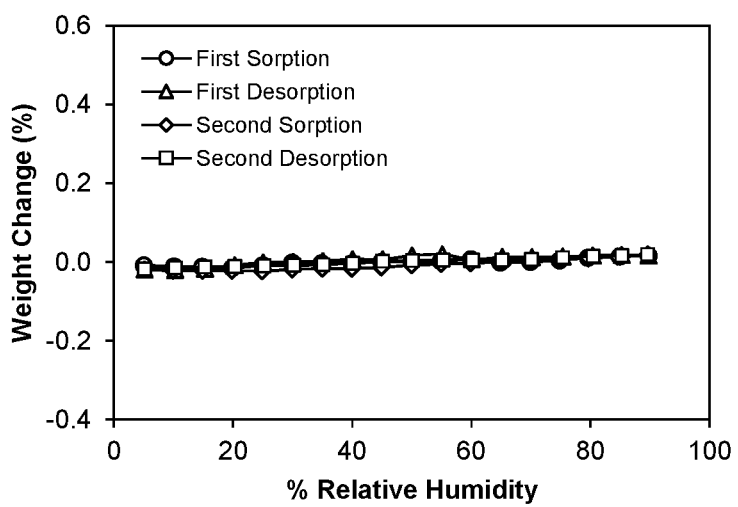
FIG. 8 shows the dynamic moisture sorption isotherm of crystalline Form II.

A representative DMS trace for Form II is shown in FIG. 8. The total moisture uptake between 5 and 90% RH was about 0.02%. Form II is non-hygroscopic.

As described in Preparation 20, Form II may be prepared by suspending compound 2-6 in a mixture of EtOH and THF, cooled to 5° C. To this suspension, $LiBH_4$ can be added. After the addition, the temperature can be increased to 10° C., and the reaction mixture can be stirred for 2 hours. The reaction can be quenched with a mixture of ammonium chloride dissolved in water. After heating to 45° C., water can be slowly added to generate crystals. The resulting slurry can be held at 45° C. for a few hours then be stirred at 15° C. and filtered. The crystalline form Form II can be rinsed with EtOH and water and then dried to give intermediate grade Form II.

This intermediate grade can be dissolved in DMSO upon heating followed by the slow addition of n-PrOH while maintaining the internal temperature at about 86° C. The mixture is stirred at about 92° C. for about 4 hours. The resulting mixture is then slowly cooled to about 20° C. and stirred at about 20° C. for a few hours. Form II may then be isolated by filtration. The crystalline Form II can be washed with nPrOH and ethanol followed by filtration.

In another aspect, the disclosure provides a method of purifying intermediate grade crystalline Form II, the method comprising: (a) dissolving intermediate grade Form II in a diluent such as DMSO and applying heating to the mixture; (b) slowly adding n-PrOH; (c) heating the mixture at about 90° C.; (d) cooling the solution to about 20° C.; and (e) isolating crystalline Form II from the reaction mixture, for example by filtration.

Pharmaceutical Compositions

Compound (I) and pharmaceutically-acceptable salts thereof are typically used in the form of a pharmaceutical composition or formulation. Compound (I) may be present as a crystalline form such as Form I or Form II. Such pharmaceutical compositions may be administered to a patient by any acceptable route of administration including, but not limited to, oral, topical (including transdermal), rectal, nasal, inhaled, and parenteral modes of administration.

Accordingly, in one of its composition aspects, the invention is directed to a pharmaceutical composition comprising a pharmaceutically-acceptable carrier or excipient and compound (I), or a pharmaceutically-acceptable salt thereof. In another composition aspect, the invention is directed to a pharmaceutical composition comprising a pharmaceutically-acceptable carrier or excipient and a crystalline form of compound (I), or a pharmaceutically-acceptable salt thereof, for example Form I or Form II. Optionally, such pharmaceutical compositions may contain other therapeutic and/or formulating agents if desired. When discussing compositions and uses thereof, the "compound of the invention" may also be referred to herein as the "active agent".

The pharmaceutical compositions of this disclosure typically contain a therapeutically effective amount of compound (I), or a pharmaceutically-acceptable salt thereof. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; including from about 5 to about 70% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture may then be shaped or loaded into tablets, capsules, pills and the like using conventional procedures and equipment.

The pharmaceutical compositions of this disclosure may be packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of this disclosure, or a pharmaceutically-acceptable salt thereof, as an active ingredient.

When intended for oral administration in a solid dosage form (i.e., as capsules, tablets, pills and the like), the pharmaceutical compositions of this disclosure will typically comprise the active agent, or a pharmaceutically acceptable salt thereof, and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of this disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of this disclosure may also be formulated to provide slow or controlled release of the active agent using, by way of example, hydroxypropyl methylcellulose in varying proportions; or other polymer matrices, liposomes and/or microspheres. In addition, the pharmaceutical compositions of this disclosure may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, or a pharmaceutically acceptable salt thereof, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compound (I), or a pharmaceutically-acceptable salt thereof, may also be administered parenterally (e.g. by intravenous, subcutaneous, intramuscular or intraperitoneal injection). For parenteral administration, the active agent, or a pharmaceutically acceptable salt thereof, is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of this disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of this disclosure will typically comprise the active ingredient, or a pharmaceutically acceptable salt thereof, and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention, or a pharmaceutically-acceptable salt thereof, and a powder suitable for use in a powder inhaler. Suitable powder bases include, by way of example, lactose or starch.

Topical Formulations

To treat skin conditions, the compound of the invention, or a pharmaceutically-acceptable salt thereof, is preferably formulated for topical administration to the skin. Topical compositions comprise fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The topical compositions useful in the subject invention can be made into a wide variety of product types. These include, but are not limited to lotions, creams, gels, sticks, sprays, ointments, pastes, foams, mousses, and cleansers. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in Remington: The Science and Practice of Pharmacy, 19th Ed. (Easton, Pa.: Mack Publishing Co., 1995). The formulation can be selected to maximize delivery to a desired target site in the body.

Lotions, which are preparations that are to be applied to the skin, or hair surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin or hair, e.g., methylcellulose, sodium carboxymethyl-cellulose, or the like.

Creams containing the active agent, or a pharmaceutically acceptable salt thereof, for delivery according to the present disclosure are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in Remington: The Science and Practice of Pharmacy, is generally a nonionic, anionic, cationic or amphoteric surfactant. Components of cream formulations may include: oil bases, such as petrolatrum, mineral oils, vegetable and animal oils, and triglycerides; cream bases, such as lanolin alcohols, stearic acid, and cetostearyl alcohol; a gel base, such as polyvinyl alcohol; solvents, such as, propylene glycol and polyethylene glycol; emulsifiers, such as polysorbates, stearates, such as glyceryl stearate, octylhydroxystearate, polyoxyl stearate, PEG stearyl ethers, isopropyl palmitate, and sorbitan monostearate; stabilizers, such as polysaccharides and sodium sulfite; emollients (i.e. moisturizers), such as medium chain triglycerides, isopropyl myristate, and dimethicone; stiffening agents, such as cetyl alcohol and stearyl alcohol; antimicrobial agents, such as methylparaben, propylparaben, phenoxyethanol, sorbic acid, diazolidinyl urea, and butylated hydroxyanisole; penetration enhancers, such as N-methylpyrrolidone, propylene glycol, polyethylene glycol monolaurate, and the like; and chelating agents, such as edetate disodium.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Water-soluble ointment bases may be prepared from polyethylene glycols of varying molecular weight; again, reference may be had to Remington: The Science and Practice of Pharmacy, supra, for further information. Suitable oily materials for use in ointment formulations include petrolatum (petroleum jelly), beeswax, cocoa butter, shea butter, and cetyl alcohol. Ointments may optionally additionally include penetration enhancers, if desired.

Useful formulations of the invention also encompass sprays. Sprays generally provide the active agent in an aqueous and/or alcoholic solution which can be misted onto the skin or hair for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin or hair, the carrier evaporates, leaving concentrated active agent at the site of administration.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

High molecular weight alcohols may be used such as cetearyl alcohol, cetyl alcohol, stearyl alcohol, emulsifying wax, glyceryl monostearate. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions.

Example of suitable nonionic emulsifying agents are described by Paul L. Lindner in "Emulsions and Emulsion", edited by Kenneth Lissant, published by Dekker, New York, N.Y., 1974. Examples of nonionic emulsifiers that may be used include but are not limited to BRIJ products such as BRIJ 2 (a polyoxyethylene (2) stearyl ether), BRIJ S20 (a polyoxyethylene (20) stearyl ether), BRIJ 72 (a polyoxyethylene (2) stearyl ether having an HLB of 4.9), BRIJ 721 (a polyoxyethylene (21) stearyl ether having an HLB of 15.5), Brij 30 (a polyoxyethylene lauryl ether having an HLB of 9.7), Polawax (emulsifying wax having an HLB of 8.0), Span 60 (sorbitan monostearate having an HLB of 4.7), Crodesta F-160 (sucrose stearate" having an HLB of 14.5).

The topical pharmaceutical compositions may also comprise suitable emollients. Emollients are materials used for the prevention or relief of dryness, as well as for the protection of the skin or hair. Useful emollients include, but are not limited to, cetyl alcohol, isopropyl myristate, stearyl alcohol, and the like. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene.

The topical pharmaceutical compositions may also comprise suitable preservatives. Preservatives are compounds added to a pharmaceutical formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel).

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid.

The topical pharmaceutical compositions may also comprise suitable viscosity increasing agents. These components are diffusible compounds capable of increasing the viscosity of a polymer-containing solution through the interaction of the agent with the polymer. Carbopol Ultrez 10 may be used as a viscosity-increasing agent.

Liquid forms, such as lotions suitable for topical administration may include a suitable aqueous or non-aqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like. Additionally, the compounds can be delivered using a sustained-release system, such as semipermeable matrices of solid hydrophobic polymers containing the therapeutic agent. Various sustained-release materials have been established and are well known by those skilled in the art.

When formulated for topical application, compound (I), or a pharmaceutically-acceptable salt thereof, may be present at between 0.1 and 50% by weight. In some embodiments, compound (I), or a pharmaceutically-acceptable salt thereof, is present at between 0.1 and 25% by weight. In some embodiments, compound (I), or a pharmaceutically-acceptable salt thereof, is present at between 0.1 and 10% by weight. In some embodiments, compound (I), or a pharmaceutically-acceptable salt thereof, is present at between 0.25 and 5% by weight. In some embodiments, compound (I), or a pharmaceutically-acceptable salt thereof, is present at between 0.25 and 2% by weight. In some embodiments, compound (I), or a pharmaceutically-acceptable salt thereof, is present at between 0.25 and 1% by weight. In some embodiments, compound (I), or a pharmaceutically-acceptable salt thereof, is present at between 0.05 and 0.5% by weight.

In some embodiments, compound (I), or a pharmaceutically-acceptable salt thereof, is present at about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.25, 3.5, 3.75, 4, 4.5, 5, 5.5, 6, 6.5, 7, 7.5, 8, 8.5, 9, 9.5 or 10% by weight.

In some embodiments, the pharmaceutical composition comprising compound (I), or a pharmaceutically-acceptable salt thereof, further comprises one or more additional therapeutic agents. In some embodiments, the one or more additional therapeutic agents is useful to treat an autoimmune skin disease. In some embodiments, the one or more additional therapeutic agents is useful to treat an inflammatory skin disease. In some embodiments, the one or more additional therapeutic agents is useful to treat atopic dermatitis. In some embodiments, the one or more additional therapeutic agents is useful to treat alopecia areata. Specific class of compounds or specific compounds that may be combined with compound (I) in a pharmaceutical composition are exemplified in later paragraphs.

The following non-limiting examples illustrate representative pharmaceutical compositions of the present invention.

Tablet Oral Solid Dosage Form

Compound (I) or a pharmaceutically-acceptable salt thereof is dry blended with microcrystalline cellulose, polyvinyl pyrrolidone, and crosscarmellose sodium in a ratio of 4:5:1:1 and compressed into tablets to provide a unit dosage of, for example, 5 mg, 20 mg or 40 mg active agent per tablet.

Capsule Oral Solid Dosage Form

Compound (I) or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Liquid Formulation

A liquid formulation comprising compound (I) or a pharmaceutically-acceptable salt thereof (0.1%), water (98.9%) and ascorbic acid (1.0%) is formed by adding a compound of the invention, or a pharmaceutically-acceptable salt thereof, to a mixture of water and ascorbic acid.

Enteric Coated Oral Dosage Form

Compound (I) or a pharmaceutically-acceptable salt thereof, is dissolved in an aqueous solution containing polyvinyl pyrrolidone and spray coated onto microcrystalline+cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Ointment Formulation for Topical Administration

Compound (I) or a pharmaceutically-acceptable salt thereof is combined with petrolatum, $C_8$-$C_{10}$ triglyceride, octylhydroxystearate, and N-methylpyrrolidone in a ratio to provide a composition containing 0.05% to 5% of active agent by weight.

Ointment Formulation for Topical Administration

Compound (I) or a pharmaceutically-acceptable salt thereof is combined with petrolatum, $C_5$-$C_{10}$ triglyceride, octylhydroxystearate, benzyl alcohol and N-methylpyrrolidone in a ratio to provide a composition containing 0.05% to 5% of active agent by weight.

Ointment Formulation for Topical Administration

Compound (I) or a pharmaceutically-acceptable salt thereof is combined with white petrolatum, propylene glycol, mono- and di-glycerides, paraffin, butylated hydroxytoluene, and edetate calcium disodium in a ratio to provide a composition containing 0.05% to 5% active agent by weight.

Ointment Formulation for Topical Administration

Compound (I) or a pharmaceutically-acceptable salt thereof is combined with mineral oil, paraffin, propylene carbonate, white petrolatum and white wax to provide a composition containing 0.05% to 5% active agent by weight.

Cream Formulation for Topical Administration

Mineral oil is combined with Compound (I) or a pharmaceutically-acceptable salt thereof, propylene glycol, isopropyl palmitate, polysorbate 60, cetyl alcohol, sorbitan monostearate, polyoxyl 40 stearate, sorbic acid, methylparaben and propylparaben to form an oil phase, which is combined with purified water by shear blending to provide a composition containing 0.05% to 5% active agent by weight.

Cream Formulation for Topical Administration

A cream formulation comprising Compound (I) or a pharmaceutically-acceptable salt thereof, benzyl alcohol, cetyl alcohol, citric acid anhydrous, mono and di-glycerides, oleyl alcohol, propylene glycol, sodium cetostearyl sulphate, sodium hydroxide, stearyl alcohol, triglycerides, and water contains 0.05% to 5% active agent by weight.

Cream Formulation for Topical Administration

A cream formulation comprising Compound (I) or a pharmaceutically-acceptable salt thereof, cetostearyl alcohol, isopropyl myristate, propylene glycol, cetomacrogol 1000, dimethicone 360, citric acid, sodium citrate, and purified water, with imidurea, methylparaben, and propylparaben, as preservatives, contains 0.05% to 5% active agent by weight.

Cream Formulation for Topical Administration

A cream formulation comprising Compound (I) or a pharmaceutically-acceptable salt thereof, stearic acid, cetostearyl alcohol, isopropyl palmitate, octylhydroxystearate, BRIJ S2 (PEG 2 Stearyl Ether), BRIJ S20 (PEG 20 Stearyl Ether), N-Methylpyrrolidine, PEG and water contains 0.05% to 5% active agent by weight.

Cream Formulation for Topical Administration

A cream formulation comprising Compound (I) or a pharmaceutically-acceptable salt thereof, stearic acid, cetostearyl alcohol, isopropyl palmitate, octylhydroxystearate, BRIJ S2 (PEG 2 Stearyl Ether), BRIJ S20 (PEG 20 Stearyl Ether), N-Methylpyrrolidine, PEG400 and water contains 0.05% to 5% active agent by weight.

Utility

Compound (I) has been shown to be a potent inhibitor of the JAK family of enzymes: JAK1, JAK2, JAK3, and TYK2. Inhibition of the family of JAK enzymes could inhibit signaling of many key pro-inflammatory cytokines. Thus Compound (I) is expected to be useful in the treatment of inflammatory diseases such as gastrointestinal inflammatory diseases, inflammatory and pruritic skin diseases, inflammatory ocular diseases and inflammatory respiratory diseases.

Inflammatory Skin Disease

Atopic dermatitis has been associated with elevation of proinflammatory cytokines that rely on the JAK-STAT pathway, in particular, IL-4, IL-5, IL-10, IL-13, and IFNγ. Since compound (I) exhibits potent inhibition at all four JAK enzymes, it is expected to potently inhibit the proinflammatory cytokines characteristic of atopic dermatitis and other inflammatory skin diseases. Compound (I) was also shown here to exhibit a $pIC_{50}$ value of 7.8 for inhibition of TSLP induced TARC in assay 4. Compound (I) exhibited a $pIC_{50}$ value of 8.5 for inhibition of IL-13 induced STAT6 phosphorylation in the cellular assays described in Assay 2. Compound (I) also exhibited a $pIC_{50}$ value of 8.3 for inhibition of IL-13 induced STAT6 phosphorylation in normal human epidermal keratinocytes in Assay 13. Furthermore, model cream and ointment formulations of compound (I) of Assay 6 have demonstrated significant compound exposure in the epidermis and dermis layers in mini-pigs without detectable plasma exposure. In an ex vivo pharmacodynamic assay using human freshly excised skin, compound (I) was shown to inhibit CXCL10 and CCL2 gene expression. Compound (I) was shown to exhibit good permeability in a human skin assay. Compound (I) also inhibited IL-31-induced production of pSTAT3 production by 80% in an in vivo model in Assay 9. Finally, compound (I) exhibited a dose-dependent effect in a TPA-induced irritant contact dermatitis model in mice in Assay 10.

Compound (I) has also been shown to exhibit a $pIC_{50}$ value of 8.4 for inhibition of IL-2 induced STAT5 phosphorylation in the cellular assays described in Assay 11, a $pIC_{50}$ value of 7.2 for inhibition of IL-12 induced STAT4 phosphorylation in human CD3+ T cells in Assay 12, a $pIC_{50}$ value of 8.4 for inhibition of IL-22 induced STAT3 phosphorylation in normal human epidermal keratinocytes in Assay 14. Finally, recovery of compound (I) for interleukin-22 (IL-22) suppressed Filaggrin expression was observed at a concentration <1 µM. IL-12, IL-22, and IL-23 are cytokines implicated in psoriasis (Baliwag et al., *Cytokine*, 2015, 73(2), 342-350 2015). These cytokines signal through JAK2 and Tyk2 enzymes (Ishizaki et al., *J. Immunol.*, 2011, 187, 181-189). Antibody therapies targeting these cytokines have demonstrated clinical utility in psoriasis (Schadler et al., *Disease-a-Month*, 2018, 1-40). A topical JAK inhibitor that can block these cytokines would be expected to be efficacious in this disease. Because these cytokines signal through Tyk2 and JAK2, Compound (I) is expected to have activity in this disease.

It is expected that sustained dermal levels of JAK inhibitors in the absence of significant systemic levels will result in potent local anti-inflammatory and anti-pruritic activity in the skin without systemically-driven adverse effects. Such compounds are expected to be beneficial in a number of dermal inflammatory or pruritic conditions that include, but are not limited to atopic dermatitis, vitiligo, cutaneous T cell lymphoma and subtypes (Sezary syndrome, mycosis fungoides, pagetoid reticulosis, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30– cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, contact dermatitis, dyshidrotic eczema, eczema, nummular dermatitis, seborrheic dermatitis, stasis dermatitis, primary localized cutaneous amyloidosis, bullous pemphigoid, skin manifestations of graft versus host disease, pemphigoid, discoid lupus, granuloma annulare, lichen simplex chronicus, pruritus, vulvar/scrotal/perianal pruritus, lichen sclerosus, post herpetic neuralgia itch, lichen planopilaris, psoriasis, and foliculitis decalvans. In particular, atopic dermatitis (Bao et al., *JAK-STAT*, 2013, 2, e24137), alopecia areata (Xing et al., *Nat Med.* 2014, 20, 1043-1049) including subtypes such as alopecia areata monolocularis, alopecia areata multilocularis, ophiasis, alopecia areata universalis, alopecia areata totalis, and alopecia areata barbae, vitiligo (Craiglow et al, *JAMA Dermatol.* 2015, 151, 1110-1112), cutaneous T cell lymphoma (Netchiporouk et al., *Cell Cycle.* 2014; 13, 3331-3335), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compound (I) may be able to alleviate associated dermal inflammation or pruritus driven by these cytokines. In particular, compound (I), or a pharmaceutically acceptable salt thereof, is expected to be useful for the treatment of atopic dermatitis and other inflammatory skin diseases.

As illustrated in Table 13, compound (I) has been shown to have high clearance in human microsomes. As such, it has the advantage of being rapidly cleared, which minimizes systemic exposure and reduces the risk of adverse effects.

As illustrated in Table 13, compound (I) also possesses high permeability which is beneficial for skin indications as it appears to be connected to better penetration in the skin.

In some embodiments, therefore, the invention provides a method of treating an inflammatory or autoimmune skin disease in a mammal (e.g., a human), comprising applying a pharmaceutical composition comprising compound (I), or a pharmaceutically acceptable salt thereof, and a pharmaceutical carrier to the skin of the mammal.

In some embodiments, the invention provides a method of treating an inflammatory or autoimmune skin disease in a mammal (e.g., a human), comprising administering compound (I), or a pharmaceutically acceptable salt thereof, to the mammal.

In some embodiments, the inflammatory skin disease is atopic dermatitis. In some embodiments, the atopic dermatitis is mild to moderate. In some embodiments, the atopic dermatitis is moderate to severe.

In some embodiments, the autoimmune skin disease is alopecia areata.

Compound (I), or a pharmaceutically acceptable salt thereof, may also be used in combination with one or more compound useful to treat inflammatory skin diseases. In some embodiments, the one or more compound is a steroid, corticosteroid, antibiotic, Histamine H1 receptor antagonist, calcineurin inhibitor, IL-13 antagonist, PDE 4 inhibitor, G-protein coupled receptor-44 antagonist, IL-4 antagonist, 5-HT 1a receptor antagonist, 5-HT 2b receptor antagonist, Alpha 2 adrenoceptor agonist, cannabinoid CB1 receptor antagonist, CCR3 chemokine, antagonist, collagenase inhibitor, cytosolic phospholipase A2 inhibitor, eotaxin ligand inhibitor, GATA 3 transcription factor inhibitor, Histamine H4 receptor antagonist, IL-10 antagonist, IL-12 antagonist, IL-17 antagonist, IL-2 antagonist, IL-23 antagonist, IL-4 receptor modulator, IL-15 antagonist, IL-6 antagonist, IL-8 antagonist, IL-9 antagonist, IL-5 antagonist, immunoglobulin E antagonist, immunoglobulin E modulator, interferon gamma receptor antagonist, Interferon gamma ligand, Interleukin 33 ligand inhibitor, Interleukin-31 receptor antagonist, Leukotriene antagonist, Liver X receptor agonist, Liver X receptor beta agonist, nuclear factor kappa B inhibitor, OX-40 receptor antagonist, PGD2 antagonist, phospholipase A2 inhibitor, SH2 domain inositol phosphatase 1 stimulator, thymic stromal lymphoprotein ligand inhibitor, TLR modulator, TNF alpha ligand modulator, TLR9 gene stimulator, cytotoxic T-lymphocyte protein-4 stimulator, opioid receptor kappa agonist, galectin-3 inhibitor, histone deacetylase-1 inhibitor, histone deacetylase-2 inhibitor, histone deacetylase-3 inhibitor, histone deacetylase-6 inhibitor, histone deacetylase inhibitor, glucocorticoid agonist, Syk tyrosine kinase inhibitor, TrkA receptor antagonist, integrin alpha-4/beta-1 antagonist, Interleukin 1 like receptor antagonist, Interleukin-1 converting enzyme inhibitor, Interleukin-31 receptor antagonist, KCNA voltage-gated potassium channel-3 inhibitor, PDE4B gene inhibitor, Kallikrein 2 inhibitor, sphingosine-1-phosphate receptor-1 agonist, retinal pigment epithelium protein stimulator, T cell surface glycoprotein CD28 inhibitor, TGF beta antagonist or vanilloid VR1 antagonist.

In some embodiments, compound (I), or a pharmaceutically acceptable salt thereof, is administered in combination with betamethasone, fucidic acid, GR-MD-02, dupilumab, rosiptor acetate, AS-101, ciclosporin, IMD-0354, secukinumab, Actimmune, lebrikizumab, CMP-001, mepolizumab, pegcantratinib, tezepelumab, MM-36, crisaborole, ALX-101, bertilimumab, FB-825, AX-1602, BNZ-1, abatacept, tacrolimus, ANB-020, JTE-052, ZPL-389, ustekinumab, GBR-830, GSK-3772847, ASN-002, remetinostat, apremilast, timapiprant, MOR-106, asivatrep, nemolizumab, fevipiprant, doxycycline, MDPK-67b, desloratadine, tralokinumab, fexofenadine, pimecrolimus, bepotastine, nalfurafine, VTP-38543, Q-301, ligelizumab, RVT-201, DMT-210, KPI-150, AKP-11, E-6005, AMG-0101, AVX-001, PG-102, ZPL-521, MEDI-9314, AM-1030, WOL-071007, MT-0814, betamethasone valerate, SB-011, epinastine, tacrolimus, tranilast, or viromed, or any combination thereof.

In some embodiments, compound (I), or a pharmaceutically acceptable salt thereof, is administered in combination with a steroid, an antibiotic and a moisturizer (Lakhani et al., *Pediatric Dermatology*, 2017, 34, 3, 322-325). In some embodiments, the one or more compound is a gram positive antibiotic, such as mupirocin or fusidic acid.

Compound (I), or a pharmaceutically-acceptable salt thereof, may also be used in combination with gram positive antibiotics, such as mupirocin and fusidic acid, to treat inflammatory skin disease. In one aspect, therefore, the invention provides a method of treating an inflammatory skin disease in a mammal, the method comprising applying a compound of the invention, or a pharmaceutically-acceptable salt thereof, and a gram positive antibiotic to the skin of the mammal. In another aspect, the invention provides a pharmaceutical composition comprising a compound of the invention, or a pharmaceutically-acceptable salt thereof, a gram positive antibiotic, and a pharmaceutically-acceptable carrier.

In another aspect, therefore, the invention provides a therapeutic combination for use in the treatment of skin inflammatory disorders, the combination comprising compound (I), or a pharmaceutically acceptable salt thereof and one or more other therapeutic agents useful for treating skin inflammatory disorders. Secondary agent(s), when included, are present in a therapeutically effective amount, i.e. in any amount that produces a therapeutically beneficial effect when co-administered with compound (I), or a pharmaceutically-acceptable salt thereof.

Also provided, therefore, is a pharmaceutical composition comprising compound (I), or a pharmaceutically salt thereof and one or more other therapeutic agents useful for treating skin inflammatory disorders.

Further, in a method aspect, the invention provides a method of treating skin inflammatory disorders, the method comprising administering to the mammal Compound (I), or a pharmaceutically acceptable salt thereof, and one or more other therapeutic agents useful for treating skin inflammatory disorders.

Gastrointestinal Inflammatory Disease

Due to its inhibition of the JAK family of enzymes, compound (I) is expected to be useful for a variety of gastrointestinal inflammatory indications that include, but are not limited to, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology*, 1996, 16, 144-150), Crohn's disease (Woywodt et al., *Eur J Gastroenterology Hepatology*, 1999, 11, 267-276), collagenous colitis (Kumawat et al., *Mol Immunology*, 2013, 55, 355-364), lymphocytic colitis (Kumawat et al., 2013), eosinophilic esophagitis (Weinbrand-Goichberg et al., *Immunol Res*, 2013, 56, 249-260), graft versus host disease-related colitis (Coghill et al., *Blood*, 2001, 117, 3268-3276), infectious colitis (Stallmach et al., *Int J Colorectal Dis*, 2004, 19, 308-315), Behcet's disease (Zhou et al., *Autoimmun Rev*, 2012, 11, 699-704), celiac disease (de Nitto et al., *World J Gastroenterol*, 2009, 15, 4609-4614), immune checkpoint inhibitor induced colitis (e.g., CTLA-4 inhibitor-induced colitis; (Yano et al., *J Translation Med*, 2014, 12, 191), PD-1- or PD-L1-inhibitor-induced colitis), and ileitis (Yamamoto et al., *Dig Liver Dis*, 2008, 40, 253-259) are characterized by elevation of certain pro-inflammatory cytokine levels. As many pro-inflammatory cytokines signal via JAK activation, compounds described in this application may be able to alleviate the inflammation and provide symptom relief.

In some embodiments, therefore, the disclosure provides a method of treating a gastrointestinal inflammatory disease in a mammal (e.g., a human), comprising administering to the mammal a pharmaceutical composition comprising a pharmaceutically-acceptable carrier and compound (I) or a pharmaceutically-acceptable salt thereof.

In some embodiments, the disclosure provides a method of treating a gastrointestinal inflammatory disease in a mammal (e.g., a human), comprising administering to the mammal compound (I), or a pharmaceutically acceptable salt thereof.

The invention further provides a method of treating ulcerative colitis in a mammal, the method comprising administering to the mammal a compound of the invention, or a pharmaceutically-acceptable salt thereof, or a pharmaceutical composition comprising a pharmaceutically-acceptable carrier and a compound of the invention, or a pharmaceutically-acceptable salt thereof.

When used to treat ulcerative colitis, the compound of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 1 to about 400 mg/day of active agent, including from about 5 to about 300 mg/day and from about 20 to about 70 mg per day of active agent for an average 70 kg human.

Compound (I), or a pharmaceutically-acceptable salt thereof, may also be used in combination with one or more agents which act by the same mechanism or by different mechanisms to effect treatment of gastrointestinal inflammatory disorders. Useful classes of agents for combination therapy include, but are not limited to, aminosalicylates, steroids, systemic immunosuppressants, anti-TNFα antibodies, anti-VLA-4 antibodies, anti-integrin $\alpha_4\beta_7$ antibodies, anti-bacterial agents, and anti-diarrheal medicines.

Aminosalicylates that may be used in combination with compound (I), include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $\alpha_4\beta_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971).

In another aspect, therefore, the invention provides a therapeutic combination for use in the treatment of gastrointestinal inflammatory disorders, the combination comprising a compound of the invention, or a pharmaceutically-acceptable salt thereof, and one or more other therapeutic agents useful for treating gastrointestinal inflammatory disorders. For example, the invention provides a combination comprising a compound of the invention, or a pharmaceutically-acceptable salt thereof, and one or more agents selected from aminosalicylates, steroids, systemic immunosuppressants, anti-TNFα antibodies, anti-VLA-4 antibodies, anti-integrin $\alpha_4\beta_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the invention, or a pharmaceutically-acceptable salt thereof.

Also provided, therefore, is a pharmaceutical composition comprising compound (I), or a pharmaceutically-acceptable salt thereof, and one or more other therapeutic agents useful for treating gastrointestinal inflammatory disorders.

Further, in a method aspect, the invention provides a method of treating gastrointestinal inflammatory disorders, the method comprising administering to the mammal Compound (I), or a pharmaceutically acceptable salt thereof, and one or more other therapeutic agents useful for treating gastrointestinal inflammatory disorders.

Respiratory Diseases

Cytokines which signal through the JAK-STAT pathway, in particular IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF) have been implicated in asthma inflammation and in other inflammatory respiratory diseases. As described above, Compound (I) has been shown to be a potent inhibitor of JAK kinases and has demonstrated potent inhibition of IL-13 pro-inflammatory cytokines in cellular assays.

The anti-inflammatory activity of JAK inhibitors has been robustly demonstrated in preclinical models of asthma (Malaviya et al., *Int Immunopharmacol,* 2010, 10, 829-836; Matsunaga et al., *Biochem and Biophys Res Commun,* 2011, 404, 261-267; Kudlacz et al., *Eur J Pharmacol,* 2008, 582, 154-161.) Accordingly, the compound (I), or a pharmaceutically acceptable salt thereof, may be useful for the treatment of inflammatory respiratory disorders such as asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. Compound (I), or a pharmaceutically acceptable salt thereof, therefore, may be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, chronic lung allograft dysfunction (CLAD), lung transplant rejections, and sarcoidosis.

In one aspect, therefore, the disclosure provides a method of treating a respiratory disease in a mammal (e.g., a human) comprising administering to the mammal compound (I), or a pharmaceutically-acceptable salt thereof.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, allergic rhinitis or sarcoidosis. In another aspect, the respiratory disease is asthma or chronic obstructive pulmonary disease.

In a further aspect, the respiratory disease is a lung infection, a helminthic infection, pulmonary arterial hypertension, sarcoidosis, lymphangioleiomyomatosis, bronchiectasis, or an infiltrative pulmonary disease. In yet another aspect, the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Loffler syndrome, bronchiolitis obliterans organizing pneumonia, or immune-checkpoint-inhibitor induced pneumonitis.

The invention further provides a method of treating a respiratory disease, the method comprising administering to the mammal a pharmaceutical composition comprising compound (I), or a pharmaceutically-acceptable salt thereof and a pharmaceutically-acceptable carrier.

Compound (I), or a pharmaceutically acceptable salt thereof, may also be used in combination with one or more compound useful to respiratory diseases.

Ocular Diseases

Many ocular diseases have been associated with elevations of proinflammatory cytokines that rely on the JAK-STAT pathway.

Compound (I), or a pharmaceutically acceptable salt thereof, therefore, may be useful for the treatment of a number of ocular diseases that include, but are not limited to, uveitis, diabetic retinopathy, diabetic macular edema, dry eye disease, age-related macular degeneration, and atopic keratoconjunctivitis.

In particular, uveitis (Horai and Caspi, *J Interferon Cytokine Res,* 2011, 31, 733-744), diabetic retinopathy (Abcouwer, *J Clin Cell Immunol,* 2013, Suppl 1, 1-12), diabetic macular edema (Sohn et al., *American Journal of Opthamology,* 2011, 152, 686-694), dry eye disease (Stevenson et al, *Arch Ophthalmol,* 2012, 130, 90-100), retinal vein occlusion (Shchuko et al, *Indian Journal of Ophthalmology,* 2015, 63(12), 905-911), and age-related macular degeneration (Knickelbein et al, *Int Ophthalmol Clin,* 2015, 55(3), 63-78) are characterized by elevation of certain pro-inflammatory cytokines that signal via the JAK-STAT pathway. Accordingly, compound (I), or a pharmaceutically acceptable salt thereof, may be able to alleviate the associated ocular inflammation and reverse disease progression or provide symptom relief.

In one aspect, therefore, the invention provides a method of treating an ocular disease in a mammal comprising administering compound (I), or a pharmaceutically-acceptable salt thereof or a pharmaceutical composition comprising compound (I), or a pharmaceutically-acceptable salt thereof and a pharmaceutical carrier to the eye of the mammal. In one aspect, the ocular disease is uveitis, diabetic retinopathy, diabetic macular edema, dry eye disease, age-related macular degeneration, or atopic keratoconjunctivitis. In one aspect, the method comprises administering compound (I), or a pharmaceutically acceptable salt thereof by intravitreal injection.

Compound (I), or a pharmaceutically acceptable salt thereof, may also be used in combination with one or more compound useful to ocular diseases.

Other Diseases

Compound (I), or a pharmaceutically acceptable salt thereof, may also be useful to treat other diseases such as other inflammatory diseases, autoimmune diseases or cancers.

Compound (I), or a pharmaceutically acceptable salt thereof, may be useful to treat oral cavities, oral mucositis and recurrent aphthous stomatitis.

Compound (I), or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

The disclosure, thereof, provides a method of treating these diseases in a mammal comprising administering compound (I), or a pharmaceutically-acceptable salt thereof or a pharmaceutical composition comprising compound (I), or a pharmaceutically-acceptable salt thereof and a pharmaceutical carrier to the mammal.

In the previous paragraphs, when used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
Bn=benzyl
Boc=tert-Butyloxycarbonyl
d=day(s)
DIPEA=N,N-diisopropylethylamine
DMF=N,N-dimethylformamide
DMSO=dimethyl sulfoxide
EtOAc=ethyl acetate
EtOH=ethyl alcohol
h=hour(s)
HATU=N,N,N',N'-tetramethyl-O-(7-azabenzotriazol-1-yl)uronium hexafluorophosphate
IPA=isopropyl alcohol
MeOH=methanol
min=minute(s)
NMP=N-methylpyrrolidone
RT=room temperature
TEA=triethylamine
THF=tetrahydrofuran
TFA=trifluoroacetic acid Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and/or mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as $CD_3OD$, $CDCl_3$, or $d_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Unless otherwise indicated the following conditions were used for preparative HPLC purifications.

Column: C18, 5 μm 21.2×150 mm or C18, 5 μm 21×250 mm or C14, 5 μm 21×150 mm
Column temperature: Room Temperature
Flow rate: 20.0 mL/min
Mobile Phases: A=Water+0.05% TFA
B=ACN+0.05% TFA,
Injection volume: (100-1500 μL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 μL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.
Analytic HPLC Conditions
Method A
Column: LUNA C18 (2), 150×4.60 mm, 3 µm
Column temperature: 37° C.
Flow rate: 1.0 mL/min
Injection volume: 5 µL
Sample preparation: Dissolve in 1:1 ACN:water
Mobile Phases: A=Water:ACN:TFA (98:2:0.05)
B=Water:ACN:TFA (2:98:0.05)
Detector wavelength: 250 nm
Gradient: 32 min total (time (min)/% B): 0/2, 10/20, 24/90, 29/90, 30/2, 32/2
Method B
Column: LUNA C18 (2), 150×4.60 mm, 3 nm
Column temperature: 37° C.
Flow rate: 1.0 mL/min
Injection volume: 10 µL
Sample preparation: Dissolve in 1:1 ACN:water
Mobile Phases: A=Water:ACN:TFA (98:2:0.05)
B=Water:ACN:TFA (10:90:0.05)
Detector wavelength: 254 nm
Gradient: 35 min total (time (min)/% B): 0/2, 20/25, 23/90, 26/90, 27/2, 35/2
Method C
Column: Poroshell 120 SB-Aq, 150 mm by 4.6 mm, 2.7 micron part #683975-914
Column temperature: 35° C.
Flow rate: 1.0 mL/min
Injection volume: 5 µL
Sample preparation: Dissolve in 50:MPB:50 MPA
Mobile Phases: A=Acetonitrile:Water:Trifluoroacetic acid (1:99:0.20)
B=Acetonitrile:Water:Trifluoroacetic acid (90:10:0.20)
Gradient:

| Time, min | % A | % B |
|---|---|---|
| 0.0 | 98.0 | 2.0 |
| 16.0 | 40.0 | 60.0 |
| 22.0 | 0.0 | 100.0 |
| 25.0 | 0.0 | 100.0 |
| 25.1 | 98.0 | 2.0 |
| 30.0 | 98.0 | 2.0 |

Preparation 1: tert-butyl ((1R,3s,5S)-9-(ethylsulfonyl)-9-azabicyclo[3.3.1]nonan-3-yl)(methyl)carbamate

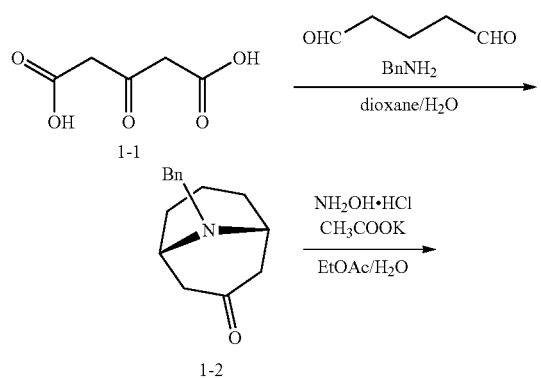

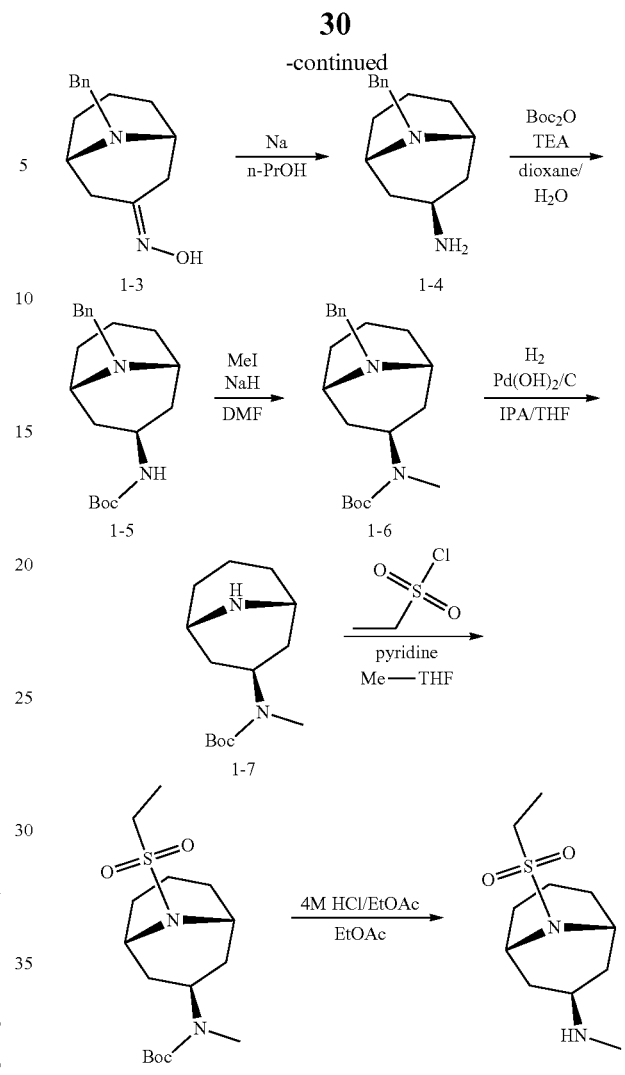

Step 1: Five reactions were carried out in parallel. To a solution of compound 1-1 (2.00 kg, 13.7 mol, 1.00 eq) in dioxane (5.00 L) and water (20.0 L) was added glutaraldehyde (2.06 kg, 20.5 mol, 1.5 eq) and phenylmethanamine (1.54 kg, 14.4 mol, 1.05 eq) drop-wise at 10° C. After addition, the reaction mixture was stirred at 20° C. for 16 h. TLC (petroleum ether:ethyl acetate=5:1, product $R_f$=0.40) and LCMS indicated the reaction was complete. The pH value of the reaction mixture was adjusted to 2 with concentrated HCl (12 N) at 20° C. After addition, the reaction mixture was heated to 60° C. and stirred for 1 h. After cooling to 10° C., ethyl acetate (10.0 L) was added to the mixture. Then the pH value of the mixture was adjusted to 10 by adding an aqueous solution of sodium hydroxide (12 N) at 10° C. The mixture was stirred for 10 min. The organic layer was separated. The aqueous layer was extracted with ethyl acetate (3.00 L). The combined organic layers were washed with brine (4.00 L), dried over sodium sulfate, and filtered. The organic layer for the five parallel reactions was combined and concentrated. The residue was purified by column chromatography (SiO$_2$, petroleum ether:ethyl acetate=30:1-2:1) to give compound 1-2 (10.0 kg, 51.5% yield, 97% purity). (m/z): [M+H]$^+$ calcd for C$_{15}$H$_{19}$NO 230.15 found 230.0. $^1$H NMR: 400 MHz DMSO-d$_6$ δ 7.24-7.41 (m, 5H), 3.88 (s, 2H), 3.20-3.21 (m, 2H), 2.73-

2.79 (m, 2H), 2.07 (d, J=16.4 Hz, 2H), 1.75-1.84 (m, 2H), 1.45-1.50 (m, 3H), 1.24-1.36 (m, 1H).

Step 2: Three reactions were carried out in parallel. To a solution of compound 1-2 (3.00 kg, 13.1 mol, 1.0 eq) in ethyl acetate (24.0 L) and water (9.00 L) was added CH3COOK (2.05 kg, 20.9 mol, 1.6 eq) and NH$_2$OH—HCl (1.82 kg, 26.2 mol, 2.0 eq) at 20° C. The suspension was heated to 45° C. and stirred for 16 h. TLC (petroleum ether:ethyl acetate=2:1, product R$_f$=0.30) and LCMS indicated the reaction was complete. The pH value of the suspension was adjusted to 8 with saturated sodium bicarbonate solution, then diluted with water (15.0 L) and ethyl acetate (10.0 L). The organic layer was separated. The aqueous layer was extracted with ethyl acetate (10.0 L×3). The organic layer of the three reactions was combined, dried over sodium sulfate, filtered and concentrated. The crude product was diluted with n-heptane (12.0 L), and stirred for 12 h. The solid was collected by filtration to give compound 1-3 (8.00 kg, 83.4% yield). (m/z): [M+H]$^+$ calcd for C$_{15}$H$_{20}$N$_2$O 245.16 found 245.1. $^1$H NMR: 400 MHz DMSO-d$_6$ 10.16 (s, 1H), 7.22-7.38 (m, 5H), 3.83 (s, 2H), 2.97 (br s, 2H), 2.87 (d, J=16.0 Hz, 1H), 2.60-2.62 (m, 1H), 2.20-2.25 (m, 1H), 2.09-2.13 (m, 1H), 1.72-1.85 (m, 3H), 1.39-1.49 (m, 3H).

Step 4: Forty-five reactions were carried out in parallel. To a solution of compound 1-3 (160 g, 655 mmol, 1.0 eq) in n-PrOH (3.20 L) at 110° C. was added Na (181 g, 7.86 mol, 12 eq) in portions over 3 h. The mixture was stirred at 110° C. for 2 h. TLC (petroleum ether:ethyl acetate=2:1, SM R$_f$=0.40) indicated the reaction was complete. The mixture was cooled to 70° C., poured into ice water (4.00 L). The aqueous layer was extracted with ethyl acetate (1.00 L×2). The combined organic layer of the forty-five reactions was washed with brine (20.0 L), dried over sodium sulfate, filtered and concentrated. The residue was diluted with n-hexane (12.0 L), stirred for 12 h. The suspension was filtered to get filtrate. The filtrate was concentrated to give compound 1-4 (6.00 kg, 88.4% yield) as a yellow oil. $^1$H NMR 400 MHz DMSO-d$_6$: δ 7.18-7.35 (m, 5H), 3.76 (s, 2H), 3.26-3.35 (m, 1H), 2.76 (s, 2H), 1.86-1.90 (m, 2H), 1.67-1.73 (m, 2H), 1.54-1.59 (m, 5H), 1.41-1.45 (m, 3H).

Step 5: Two reactions were carried out in parallel. To a solution of compound 1-4 (2.10 kg, 9.12 mol, 1.1 eq) in dioxane (12.6 L) and water (1.26 L) was added Et$_3$N (1.01 kg, 10.0 mol, 1.1 eq) and (Boc)$_2$O (2.19 kg, 10.0 mol, 1.1 eq) drop-wise at 0° C., with the temperature below 20° C. The mixture was heated to 40° C. and stirred for 10 h. TLC (petroleum ether:ethyl acetate=2:1, product R$_f$=0.40) showed the reaction was complete. The mixture was cooled to 10° C., filtered to get filter cake. The filtrate was concentrated. The filter cake was washed with n-hexane (3.00 L) to give compound 1-5 (4.00 kg, 66.4% yield) as a white solid. $^1$H NMR: 400 MHz DMSO-d$_6$: δ 7.28-7.33 (m, 4H), 7.19-7.22 (m, 1H), 6.64 (d, J=8.0 Hz, 1H), 4.10-4.17 (m, 1H), 3.77 (s, 2H), 2.77 (s, 2H), 1.88-1.90 (m, 2H), 1.72-1.75 (m, 3H), 1.57-1.61 (m, 3H), 1.43-1.48 (m, 2H), 1.38 (s, 9H).

Step 6: Four reactions were carried out in parallel. To a suspension of compound 1-5 (1.50 kg, 4.54 mol, 1.0 eq) in DMF (13.5 L) was added NaH (272 g, 6.81 mol, 60% purity, 1.5 eq) portion-wise at 0° C. under N$_2$. The suspension was naturally warmed to 25° C. and stirred for 30 min. After it was cooled down to 0° C., MeI (773 g, 5.45 mol, 1.2 eq) was added drop-wise to the suspension. The reaction mixture was naturally warmed to 25° C. and stirred for 12 h. TLC (petroleum ether:ethyl acetate=5:1, product R$_f$=0.50) and LCMS showed the reaction was complete. The mixture was poured into ice water (30.0 L), extracted with ethyl acetate (9.00 L, 3.00 L). The combined organic layer of the four reactions was washed with ice water (20.0 L), brine (10.0 L), dried over sodium sulfate, filtered and concentrated to give compound 1-6 (6.00 kg, crude) as a yellow oil. The crude product was used for the next step. $^1$H NMR: 400 MHz DMSO-d$_6$ δ 7.21-7.37 (m, 5H), 4.87 (br s, 1H), 3.80 (s, 2H), 2.86 (s, 2H), 2.68 (s, 3H), 1.64-1.99 (m, 6H), 1.40-1.49 (m, 13H). (m/z): [M+H]$^+$ calcd for C$_{21}$H$_{32}$N$_2$O$_2$ 344.25 found 345.2.

Step 7: Thirty-nine reactions were carried out in parallel. To a solution of compound 1-6 (150 g, 435 mmol, 1.0 eq) in IPA (500 mL) and THF (500 mL) was added Pd(OH)$_2$/C (70 g, 40% purity). The suspension was degassed under vacuum and purged with H2 several times. The mixture was stirred under H2 (50 psi) at 25° C. for 16 h. TLC (petroleum ether:ethyl acetate=5:1, SM R$_f$=0.50) and LCMS indicated the reaction was complete. The thirty-nine reactions were combined. The mixture was filtered to get filtrate. The filter cake was washed with IPA/THF (1:1, 25.0 L). The combined filtrate was concentrated to give compound 1-7 (3.85 kg, crude) as a light yellow oil. The crude product was used for the next step directly. (m/z): [M+H]$^+$ calcd for C$_{14}$H$_{26}$N$_2$O$_2$ 255.20 found 255.1. $^1$H NMR: 400 MHz DMSO-d$_6$ δ 4.88 (br s, 1H), 3.08 (s, 2H), 2.60 (s, 3H), 1.73-1.76 (m, 5H), 1.51-1.61 (m, 5H), 1.39 (s, 9H).

Step 8: Four reactions were carried out in parallel. To a solution of compound 1-7 (750 g, 2.95 mol, 1.0 eq) in 2-methyl tetrahydrofuran (3.00 L) was added pyridine (466 g, 5.90 mol, 2.0 eq) and ethanesulfonyl chloride (398 g, 3.10 mol, 1.05 eq) drop-wise at 0° C. under N$_2$. The mixture was warmed to 25° C. and stirred for 3 h. TLC (petroleum ether:ethyl acetate=2:1, product R$_f$=0.50) indicated the reaction was complete. The four reactions were combined. The mixture was quenched with ice water (10.0 L). The organic layer was separated, washed with 0.5 N HCl (3.00 L×2). The combined aqueous layer was extracted with ethyl acetate (3.00 L), the organic layer was washed with 0.5 N HCl (500 mL) again. The combined organic layer was washed with brine (5.00 L), dried over sodium sulfate, filtered and concentrated to give compound 1-8 (2.20 kg, crude) as a yellow oil. The crude product was used in the next step. $^1$H NMR: 400 MHz DMSO-d$_6$ δ 4.94 (br s, 1H), 3.98 (s, 2H), 3.10 (q, J=7.2 Hz, 2H), 2.58 (s, 3H), 1.83-1.91 (m, 5H), 1.56-1.71 (m, 5H), 1.40 (s, 9H), 1.19 (t, J=7.2 Hz, 3H).

Step 9: Four reactions were carried out in parallel. To a solution of compound 1-8 (550 g, 1.59 mol, 1.0 eq) in EtOAc (2.75 L) was added HCl/EtOAc (4 M, 3.0 eq) drop-wise at 25° C. The mixture was stirred at 25° C. for 12 h. TLC (petroleum ether:ethyl acetate=2:1, SM R$_f$=0.50) showed the reaction was complete. The four reactions were combined. The mixture was filtered to get filter cake to give compound 1-9 (1.25 kg, crude, HCl) as a yellow solid. $^1$H NMR: 400 MHz DMSO-d$_6$ δ 9.04 (s, 1H), 4.02 (s, 2H), 3.88-3.94 (m, 1H), 3.09 (q, J=7.2 Hz, 2H), 2.09-2.14 (m, 2H), 1.61-1.84 (m, 8H), 1.19 (t, J=7.2 Hz, 3H).

Preparation 2: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol (I)

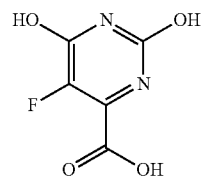

2-1

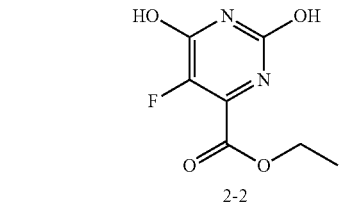

2-2

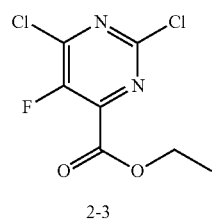

2-3

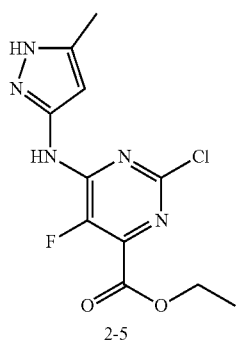

2-5

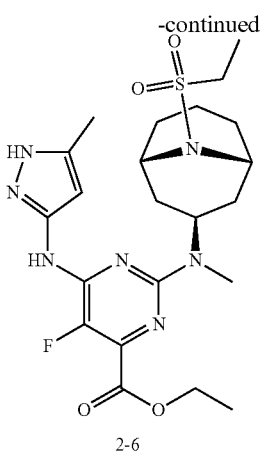

2-6

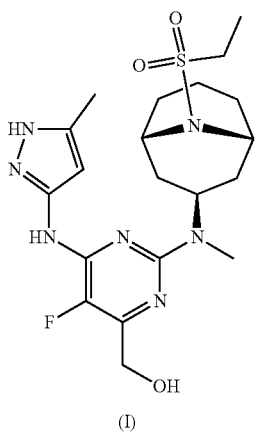

(I)

Step 1: A solution of compound 2-1 (1.00 kg, 5.74 mol, 1.0 eq) in ethanol (15.0 L) with saturated HCl (1.40 kg, 38.4 mol) was stirred at 90° C. for 60 h. HPLC showed one main peak was detected. The reaction mixture was filtered. The filter cake was collected to give compound 2-2 (1.00 kg, 81.8% yield, 98.8% purity) as a white solid. $^1$H NMR: 400 MHz DMSO-$d_6$ δ 11.82 (br s, 1H), 10.82 (br s, 1H), 4.31 (q, J=7.2 Hz, 2H), 1.27 (t, J=6.8 Hz, 3H).

Step 2: Five reactions were carried out in parallel. To a solution of compound 2-2 (560 g, 2.77 mol, 1.0 eq) in POCl$_3$ (1.68 L) was added N, N-diethylaniline (289 g, 1.94 mol, 0.7 eq). The mixture was stirred at 140° C. for 12 h. TLC (petroleum ether:ethyl acetate=10:1, product R$_f$=0.50) indicated compound 2-2 was consumed completely. The five reactions were combined. The reaction mixture was concentrated under reduced pressure to give a residue. The residue was diluted with ethyl acetate (25.0 L). The solution was poured into crushed ice (25.0 L). The water phase was extracted with ethyl acetate (25.0 L). The combined organic layers were washed with saturated sodium carbonate solution (10.0 L×2), dried over sodium sulfate, filtered and concentrated under reduced pressure to give a residue. The residue was purified by column chromatography (SiO$_2$, petroleum ether:ethyl acetate=1:0-50:1) to give compound 2-3 (2.00 kg) as a brown liquid. $^1$H NMR: 400 MHz CDCl$_3$ δ 4.51 (q, J=7.2 Hz, 2H), 1.44 (t, J=7.2 Hz, 3H).

Step 3: Four reactions were carried out in parallel. A mixture of compound 2-3 (480 g, 2.01 mol, 1.0 eq), compound 2-4 (224 g, 2.31 mol, 1.15 eq), DIPEA (519 g, 4.02 mol, 2.0 eq) in ethanol (2.60 L) was degassed and purged with N$_2$ for 3 times, and then the mixture was stirred at 25° C. for 4 h under N$_2$ atmosphere. TLC (petroleum ether:ethyl acetate=10:1) indicated compound 2-3 was consumed completely. TLC (petroleum ether:ethyl acetate=1:1, product $R_f$=0.40) indicated one new spot formed. The four reactions were combined. The reaction mixture was filtered and the filter cake was collected. The filtrate was concentrated under reduced pressure to give a residue. The residue was triturated with water (38.0 L) and filtered. The filter cake (300 g) was triturated with ethanol (600 mL) and filtered. The two filter cakes were combined to give compound 2-5 (1.50 kg, 62.2% yield) as a yellow solid. $^1$H NMR: 400 MHz DMSO-$d_6$ δ 12.31 (s, 1H), 10.76 (s, 1H), 6.38 (s, 1H), 4.35 (q, J=7.2 Hz, 2H), 2.27 (s, 3H), 1.30 (t, J=7.2 Hz, 3H).

Step 4: Four reactions were carried out in parallel. A solution of compound 2-5 (254 g, 848 mmol, 1.0 eq), compound 1-9 (300 g, 1.06 mol, HCl, 1.25 eq) and DIPEA (548 g, 4.24 mol, 5.0 eq) in DMSO (600 mL) was stirred at 130° C. for 16 h. TLC (ethyl acetate:petroleum ether=2:1, $R_f$=0.30) and LCMS showed ~9% of the starting material remained. The mixture was cooled to 25° C. The four reactions were combined, poured into ice water (12.0 L). A yellow precipitate was formed. The solid was collected by filtration to give compound 2-6 (1.50 kg, ~76% purity) as a yellow solid. (m/z): [M+H]$^+$ calcd for $C_{22}H_{32}FN_7O_4S$ 510.22 found 510.2.

A suspension of compound 2-6 (440 g, 656 mmol, ~76% purity) in ethanol (1.10 L) was heated to 95° C. until the solid was dissolved. The solution was cooled to 25° C. and stirred for 12 h. HPLC showed ~96.9% purity. The three reactions were combined. The suspension was filtered to get the filter cake to give compound 2-6 (~570 g, 96.9% purity) as a light yellow solid. The product was used for the next step directly. $^1$H NMR: 400 MHz DMSO-$d_6$ δ 12.12 (s, 1H), 9.73 (s, 1H), 6.35 (s, 1H), 5.59 (br s, 1H), 4.32 (m, 2H), 4.02 (s, 2H), 3.13 (q, J=7.2 Hz, 2H), 2.83 (s, 3H), 2.20 (s, 3H), 1.94 (s, 3H), 1.64-1.73 (m, 5H), 1.76-1.87 (m, 5H), 1.29 (t, J=7.2 Hz, 3H), 1.21 (t, J=7.2 Hz, 3H).

Step 5: Five reactions were carried out in parallel. To a solution of compound 2-6 (130 g, 255 mmol, 1.0 eq) in tetrohydrofuran (3.25 L) and ethanol (3.25 L) was added NaBH$_4$ (77.2 g, 2.04 mol, 8.0 eq) and CaCl$_2$) (113 g, 1.02 mol, 4.0 eq) portion-wise at 0° C. The mixture was warmed to 10° C. and stirred for 2 h. TLC (ethyl acetate:petroleum ether=3:1, product $R_f$=0.20) showed the reaction was complete. The five reactions were combined. The mixture was quenched by saturated sodium carbonate solution (6.00 L), diluted with ethyl acetate (15.0 L) and stirred for 0.5 h. The suspension was filtered to get filtrate. The organic layer was separated, and aqueous layer was extracted with ethyl acetate (5.00 L×2). The combined organic layer was washed with brine (5.00 L), dried over sodium sulfate, filtered and concentrated to give (I) (500 g, crude) as a light yellow solid.

Purification: Five reactions were carried out in parallel. A suspension of I (100 g, 210 mmol) in ethanol (3.00 L) was heated to 95° C. until the solid was dissolved. The solution was cooled to 25° C. and stirred for 12 h, a lot of precipitate formed. HPLC showed 100% purity. The five reactions were combined. The solid was collected by filtration to give a total of 330 g of compound I (99.3% purity) as a light yellow solid (crystalline Form I). (m/z): [M+H]$^+$ calcd for $C_{20}H_{30}FN_7O_3S$ 468.21 found 468.3. $^1$H NMR: 400 MHz DMSO-$d_6$ δ 12.02 (s, 1H), 9.29 (s, 1H), 6.34 (s, 1H), 5.61 (br s, 1H), 5.02 (t, J=6.8 Hz, 1H), 4.33 (d, J=4.0 Hz, 2H), 4.02 (s, 2H), 3.12 (q, J=7.2 Hz, 2H), 2.84 (s, 3H), 2.19 (s, 3H), 1.82-2.01 (m, 3H), 1.63-1.74 (m, 5H), 1.21 (t, J=7.2 Hz, 3H).

Preparation 3: ethyl 5-fluoro-2,6-dihydroxypyrimidine-4-carboxylate

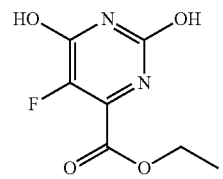

A solution of 5-fluoro-2,6-dihydroxypyrimidine-4-carboxylic acid (20.4 g, 120 mmol) in DMF (200 mL) was treated with DBU (18.7 g, 123 mmol) and was stirred for 0.5 h at 25° C. Then EtI (19.2 g, 123 mmol) was added and the resulting solution was heated to 60° C. for 3 hours. H$_2$O (1000 mL) was added to the mixture, and the resulting precipitate was collected by filtration, washed with H$_2$O (200 mL), and dried to give ethyl 5-fluoro-2,6-dihydroxypyrimidine-4-carboxylate (19 g, 80% yield).

Preparation 4: ethyl 2,6-dichloro-5-fluoropyrimidine-4-carboxylate

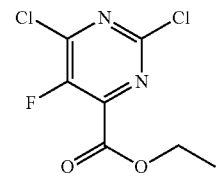

A mixture of ethyl 5-fluoro-2,6-dihydroxypyrimidine-4-carboxylate (5 g, 24.8 mmol), PhNEt$_2$ (2.58 g, 17.3 mmol), POCl$_3$ (130 g, 855.9 mmol) was heated to 100° C. for 4 hours. Then the reaction mixture was cooled to room temperature and poured into ice water (500 mL). The aqueous layer was extracted with EtOAc (1000 mL) and the organic layer was washed with sat. NaHCO$_3$ (200 mL), brine (200 mL), dried over Na$_2$SO$_4$, filtered, and concentrated under vacuum. The residue was purified by column chromatography (80 g column; 0-50% EtOAc in hexanes) to give ethyl 2,6-dichloro-5-fluoropyrimidine-4-carboxylate as yellow oil (3.8 g, 65%).

Preparation 5: ethyl 2-chloro-5-fluoro-6-((5-methyl-1H-pyrazol-3-yl)amino)pyrimidine-4-carboxylate

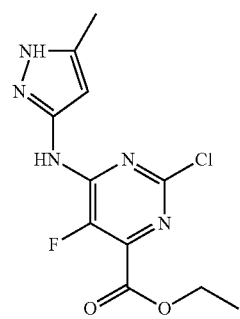 [SMILES: CCOC(=O)c1nc(Cl)nc(Nc2cc(C)[nH]n2)c1F]

A mixture of ethyl 2,6-dichloro-5-fluoropyrimidine-4-carboxylate (3.8 g, 16 mmol), 5-methyl-1H-pyrazol-3-amine (1.86 g, 19 mmol), and DIPEA (4 g, 32 mmol) in EtOH (100 mL) was stirred at r.t. for 2 h. The reaction mixture was concentrated under vacuum. Then water (500 mL) was added and the reaction mixture was filtered and the filter cake was washed with 100 mL of H2O, and dried in vacuo to give ethyl 2-chloro-5-fluoro-6-((5-methyl-1H-pyrazol-3-yl)amino)pyrimidine-4-carboxylate (3.8 g 80% yield).

Preparation 6: tert-butyl (1R,3s,5S)-3-((4-(ethoxycarbonyl)-5-fluoro-6-((5-methyl-1H-pyrazol-3-yl)amino)pyrimidin-2-yl)(methyl)amino)-9-azabicyclo[3.3.1]nonane-9-carboxylate

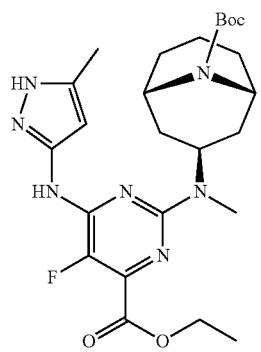 [SMILES: CCOC(=O)c1nc(N(C)[C@@H]2C[C@H]3CCC[C@@H](C2)N3C(=O)OC(C)(C)C)nc(Nc2cc(C)[nH]n2)c1F]

A mixture of ethyl 2-chloro-5-fluoro-6-((5-methyl-1H-pyrazol-3-yl)amino)pyrimidine-4-carboxylate (1.7 g, 5.684 mmol), tert-butyl (1R,3s,5S)-3-(methylamino)-9-azabicyclo[3.3.1]nonane-9-carboxylate (2.17 g, 8.527 mmol), and DIPEA (1.47 g, 11.368 mmol) in DMSO (50 mL) was heated to 110° C. for 18 h. The reaction mixture was poured into water (200 mL) and the reaction mixture was filtered and the filter cake was washed with 200 mL of H$_2$O and dried in vacuum to give crude tert-butyl(1R,3s,5S)-3-((4-(ethoxycarbonyl)-5-fluoro-6-((5-methyl-1H-pyrazol-3-yl)amino)pyrimidin-2-yl)(methyl)amino)-9-azabicyclo[3.3.1]nonane-9-carboxylate (3.5 g, crude). (m/z): [M+H]$^+$ calcd for C$_{25}$H$_{37}$FN$_7$O$_4$ 518.29 found 518.2.

Preparation 7: tert-butyl (1R,3s,5S)-3-((5-fluoro-4-(hydroxymethyl)-6-((5-methyl-1H-pyrazol-3-yl)amino)pyrimidin-2-yl)(methyl)amino)-9-azabicyclo[3.3.1]nonane-9-carboxylate

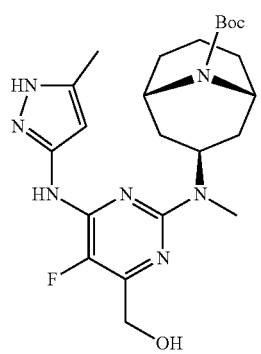 [SMILES: Cc1cc(Nc2nc(N(C)[C@@H]3C[C@H]4CCC[C@@H](C3)N4C(=O)OC(C)(C)C)nc(CO)c2F)n[nH]1]

A mixture of tert-butyl(1R,3s,5S)-3-((4-(ethoxycarbonyl)-5-fluoro-6-((5-methyl-1H-pyrazol-3-yl)amino)pyrimidin-2-yl)(methyl)amino)-9-azabicyclo[3.3.1]nonane-9-carboxylate (3.5 g, 7 mmol), NaBH$_4$ (2.1 g, 56 mmol), and CaCl$_2$ (3.1 g, 28 mmol) in a mixture of EtOH (50 mL) and THF (50 mL) was stirred overnight at 25° C. The reaction mixture was quench with Na$_2$CO3 (aq) (80 mL) and H$_2$O (80 mL), the aqueous layer was extracted with EtOAc (100 mL×3) and the combined organic layers were washed with brine, dried over Na$_2$SO$_4$, and concentrated under vacuum. The residue was purified by prep-HPLC to give tert-butyl (1R,3s,5S)-3-45-fluoro-4-(hydroxymethyl)-6-((5-methyl-1H-pyrazol-3-yl)amino)pyrimidin-2-yl)(methyl)amino)-9-azabicyclo[3.3.1]nonane-9-carboxylate (1.4 g, 44%). (m/z): [M+H]$^+$ calcd for C$_{23}$H$_{35}$FN$_7$O$_3$ 476.28 found 476.3.

Preparation 8: (2-(((1R,3s,5S)-9-azabicyclo[3.3.1]nonan-3-yl)(methyl)amino)-5-fluoro-6-((5-methyl-1H-pyrazol-3-yl)amino)pyrimidin-4-yl)methanol

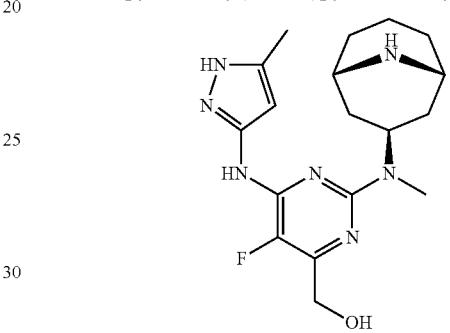

A solution of tert-butyl(1R,3s,5S)-3-((5-fluoro-4-(hydroxymethyl)-6-((5-methyl-1H-pyrazol-3-yl)amino)pyrimidin-2-yl)(methyl)amino)-9-azabicyclo[3.3.1]nonane-9-carboxylate (1.4 g, 2.95 mmol) in HCl/dioxane (50 mL) was stirred at 25° C. for 4 h. The reaction mixture was filtered and the filter cake was washed with 100 mL of EtOAc and dried in vacuum to give (2-(((1R,3s,5S)-9-azabicyclo[3.3.1]nonan-3-yl)(methyl)amino)-5-fluoro-6-((5-methyl-1H-pyrazol-3-yl)amino)pyrimidin-4-yl)methanol (1.4 g, 100%). (m/z): [M+H]$^+$ calcd for C$_{18}$H$_{27}$FN$_7$O 376.23 found 376.2.

Preparation 9: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol

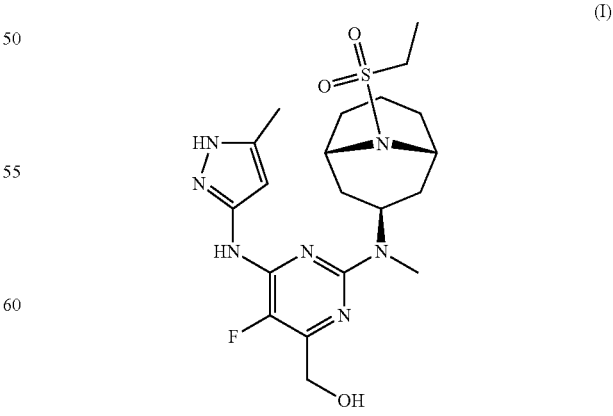

(I)

(2-((1R,3s,5S)-9-azabicyclo[3.3.1]nonan-3-yl(methyl)amino)-5-fluoro-6-((5-methyl-1H-pyrazol-3-yl)amino)pyrimidin-4-yl)methanol (95 mg, 0.253 mmol) was dissolved in Pyridine (4.0 ml) and treated with ethanesulfonyl chloride (0.024 ml, 0.253 mmol). The reaction mixture was stirred for 2 hours and subsequently concentrated in vacuo. The crude residue was dissolved in 3 mL of a 1:1 mixture of acetic acid/water, filtered to remove particulate, and purified by preparative HPLC (Agilent Dynamax 250×21.4 mm 10 μm, 15 mL/min, 2-50% ACN+0.05% TFA/ACN) using a 2-50% gradient of ACN in water with 0.05% TFA). Pure fractions were combined and lyophilized to provide the TFA salt of the title compound (12.92 mg, 8.8% yield, 99.9% purity). (m/z): [M+H]+ calcd for $C_{20}H_{31}FN_7O_3S$ 468.22 found 468.

Preparation 10: methyl 2-chloro-6-((5-methyl-1H-pyrazol-3-yl)amino)pyrimidine-4-carboxylate

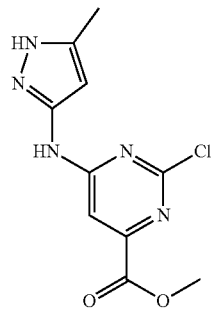 [SMILES: COC(=O)c1cc(Nc2cc(C)[nH]n2)nc(Cl)n1]

A mixture of 5-methyl-1H-pyrazol-3-amine (5.6 g, 58 mmol), methyl 2,6-dichloropyrimidine-4-carboxylate (12.0 g, 58 mmol), and DIPEA (15.0 g, 116 mmol) in DMSO (120 ml) was stirred at 25° C. for 12 hours. H₂O (500 mL) was added and the precipitated solid was collected by filtration to give the title intermediate (15 g, 97%) as a yellow solid. (m/z): [M+H]+ calcd for $C_{10}H_{11}ClN_5O_2$ 268.05 found 268.1.

Preparation 11: tert-butyl (1R,3s,5S)-3-((4-(methoxycarbonyl)-6-((5-methyl-1H-pyrazol-3-yl)amino)pyrimidin-2-yl)(methyl)amino)-9-azabicyclo[3.3.1]nonane-9-carboxylate

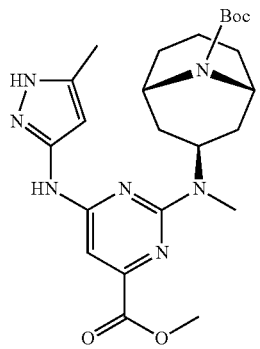 [SMILES: COC(=O)c1cc(Nc2cc(C)[nH]n2)nc(N(C)[C@@H]2C[C@H]3CCC[C@@H](C2)N3C(=O)OC(C)(C)C)n1]

A mixture of methyl 2-chloro-6-((5-methyl-1H-pyrazol-3-yl)amino)pyrimidine-4-carboxylate (12.0 g, 45 mmol), tert-butyl (1R,3s,5S)-3-(methylamino)-9-azabicyclo[3.3.1]nonane-9-carboxylate (13.7 g, 54 mmol), and DIPEA (12.0 g, 90 mmol) in NMP (120 ml) was stirred at 120° C. for 16 hours. The reaction was poured into H₂O (2000 mL), the precipitated solid was collected by filtration to give the title intermediate (15 g, 68%) as a white solid. (m/z): [M+H]+ calcd for $C_{24}H_{36}N_7O_4$ 486.28 found 486.3.

Preparation 12: tert-butyl (1R,3s,5S)-3-((4-carbamoyl-6-((5-methyl-1H-pyrazol-3-yl)amino)pyrimidin-2-yl)(methyl)amino)-9-azabicyclo[3.3.1]nonane-9-carboxylate

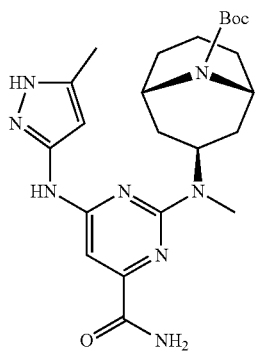 [SMILES: Cc1cc(Nc2cc(C(N)=O)nc(N(C)[C@@H]3C[C@H]4CCC[C@@H](C3)N4C(=O)OC(C)(C)C)n2)n[nH]1]

To tert-butyl (1R,3s,5S)-3-((4-(methoxycarbonyl)-6-((5-methyl-1H-pyrazol-3-yl)amino)pyrimidin-2-yl)(methyl)amino)-9-azabicyclo[3.3.1]nonane-9-carboxylate (3 batches of 2 g, 4.12 mmol) was added NH3/MeOH (3 aliquots of 60 ml) in a 100 ml sealed tube, the reaction mixture was stirred at 25° C. for 12 hours. The reaction mixture was concentrated in vacuum to afford the title intermediate (3.7 g, 64%). (m/z): [M+H]+ calcd for $C_{23}H_{35}N_8O_3$ 471.28 found 471.3.

Preparation 13: 2-(((1R,3s,5S)-9-azabicyclo[3.3.1]nonan-3-yl)(methyl)amino)-6-((5-methyl-1H-pyrazol-3-yl)amino)pyrimidine-4-carboxamide

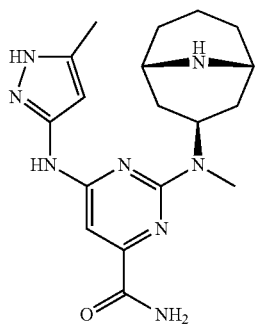 [SMILES: Cc1cc(Nc2cc(C(N)=O)nc(N(C)[C@@H]3C[C@H]4CCC[C@@H](C3)N4)n2)n[nH]1]

To a mixture of tert-butyl(1R,3s,5S)-3-((4-carbamoyl-6-((5-methyl-1H-pyrazol-3-yl)amino)pyrimidin-2-yl)(methyl)amino)-9-azabicyclo[3.3.1]nonane-9-carboxylate (3.7 g, 7.9 mmol) in dioxane (185 mL) was added HCl/Dioxane (37 mL). The reaction was stirred at 25° C. for 3 hours. TLC showed no starting material remained. The solvent was removed, and the crude product was washed with ethyl acetate/MeOH (100:1) to give the title intermediate as the HCl salt (4.0 g, 95%). (m/z): [M+H]+ calcd for $C_{18}H_{27}N_8O$ 371.23 found 371.1.

Preparation 14: 2-(((1R,3s,5S)-9-(ethylsulfonyl)-9-azabicyclo[3.3.1]nonan-3-yl)(methyl)amino)-6-((5-methyl-1H-pyrazol-3-yl)amino)pyrimidine-4-carboxamide (C-1)

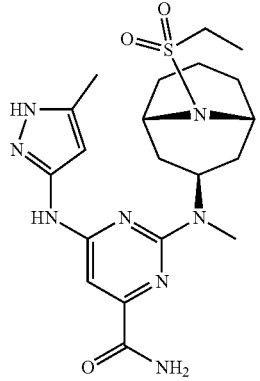 [SMILES: CCS(=O)(=O)N1[C@@H]2CCC[C@H]1C[C@H](N(C)c1nc(Nc3cc(C)[nH]n3)cc(C(N)=O)n1)C2]

2-((1R,3s,5S)-9-azabicyclo[3.3.1]nonan-3-yl(methyl)amino)-6-((5-methyl-1H-pyrazol-3-yl)amino)pyrimidine-4-carboxamide (40 mg, 0.108 mmol) and DIPEA (0.057 ml, 0.324 mmol) were dissolved in DMF (1.50 ml) and cooled to 0° C. Ethane sulfonyl chloride was added and the reaction mixture was allowed to warm to room temperature and stirred for 72 hours. The reaction mixture was concentrated in vacuo and crude product was purified by preparative reverse phase HPLC (Agilent Dynamax 250×21.4 mm 10 μm, 15 mL/min, 2-70% ACN+0.1% TFA/ACN) to provide the TFA salt of the title compound (4.5 mg, 9.01%). (m/z): [M+H]$^+$ calcd for $C_{20}H_{31}N_8O_3S$ 463.22 found 463.2.

Preparation 15: methyl 2-chloro-6-((5-methyl-1H-pyrazol-3-yl)amino)pyrimidine-4-carboxylate

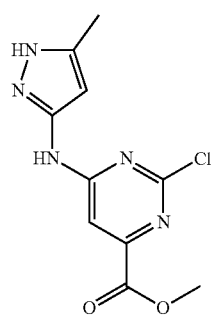 [SMILES: COC(=O)c1cc(Nc2cc(C)[nH]n2)nc(Cl)n1]

A mixture of 5-methyl-1H-pyrazol-3-amine (5.6 g, 58 mmol), methyl 2,6-dichloropyrimidine-4-carboxylate (12.0 g, 58 mmol), and DIPEA (15.0 g, 116 mmol) in DMSO (120 ml) was stirred at 25° C. for 12 hours. H$_2$O (500 mL) was added and the precipitated solid was collected by filtration to give the title compound (15 g, 97%). (m/z): [M+H]$^+$ calcd for $C_{10}H_{11}ClN_5O_2$ 268.05 found 268.1.

Preparation 16: tert-butyl (1R,3s,5S)-3-((4-(methoxycarbonyl)-6-((5-methyl-1H-pyrazol-3-yl)amino)pyrimidin-2-yl)(methyl)amino)-8-azabicyclo[3.2.1]octane-8-carboxylate

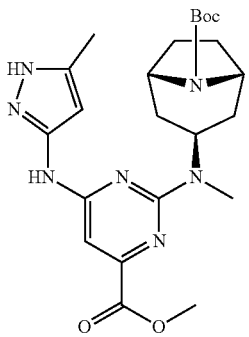 [SMILES: COC(=O)c1cc(Nc2cc(C)[nH]n2)nc(N(C)[C@@H]2C[C@H]3CC[C@@H](C2)N3C(=O)OC(C)(C)C)n1]

A mixture of methyl 2-chloro-6-((5-methyl-1H-pyrazol-3-yl)amino)pyrimidine-4-carboxylate (8.3 g, 31.0 mmol), tert-butyl (1R,3s,5S)-3-(methylamino)-8-azabicyclo[3.2.1]octane-8-carboxylate (8.2 g, 34.1 mmol), and DIPEA (10.8 mL, 62.0 mmol) in DMSO (85 ml) was stirred at 120° C. for 16 hours. The mixture was poured into 2 L of water, stirred vigorously, and then filtered to afford the title compound (11.1 g, 76%). (m/z): [M+H]$^+$ calcd for $C_{23}H_{34}N_7O_4$ 472.27 found 472.3.

Preparation 17: tert-butyl (1R,3s,5S)-3-((4-(hydroxymethyl)-6-((5-methyl-1H-pyrazol-3-yl)amino)pyrimidin-2-yl)(methyl)amino)-8-azabicyclo[3.2.1]octane-8-carboxylate

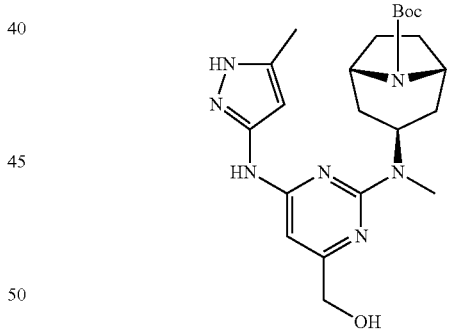

To a mixture of NaBH$_4$ (8 g, 212 mmol) in MeOH (100 mL) was added tert-butyl (1R,3s,5S)-3-((4-(methoxycarbonyl)-6-((5-methyl-1H-pyrazol-3-yl)amino)pyrimidin-2-yl)(methyl)amino)-8-azabicyclo[3.2.1]octane-8-carboxylate (10 g, 21.2 mmol) in THF (100 mL) at 0° C. The reaction mixture was then heated to reflux for 1 h. The reaction was quenched with water (500 mL), and the mixture extracted with ethyl acetate (3×200 mL). The combined organic layers were washed with brine (1×100 mL), dried over anhydrous Na$_2$SO$_4$, and concentrated in vacuo. The crude residue was purified by flash chromatography on silica gel (Petroleum ether:ethyl acetate=4:1) to afford the title compound (7 g, 68%). (m/z): [M+H]$^+$ calcd for $C_{22}H_{34}N_7O_3$ 444.27 found 444.3.

Preparation 18: (2-(((1R,3s,5S)-8-azabicyclo[3.2.1]
octan-3-yl)(methyl)amino)-6-((5-methyl-1H-pyrazol-3-yl)amino)pyrimidin-4-yl)methanol

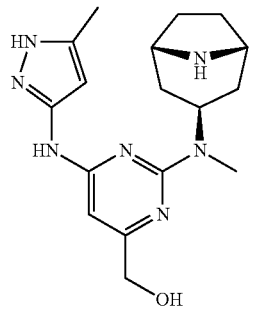 [SMILES: Cc1cc(Nc2cc(CO)nc(N(C)[C@@H]3C[C@H]4CC[C@@H](C3)N4)n2)n[nH]1]

A mixture of tert-butyl(1R,3s,5S)-3-((4-(hydroxymethyl)-6-((5-methyl-1H-pyrazol-3-yl)amino)pyrimidin-2-yl)(methyl)amino)-8-azabicyclo[3.2.1]octane-8-carboxylate (6.5 g, 14.7 mmol) in HCl/dioxane (100 mL) was stirred at r.t. for 1 h. The mixture was concentrated in vacuum to afford the HCl salt of the title intermediate (4.8 g, 100%). (m/z): [M+H]$^+$ calcd for $C_{17}H_{26}N_7O$ 344.22 found 344.1.

Preparation 19: 3-41R,3s,5S)-3-((4-(hydroxymethyl)-6-((5-methyl-1H-pyrazol-3-yl)amino)pyrimidin-2-yl)(methyl)amino)-8-azabicyclo[3.2.1]octan-8-yl)propanenitrile (C-2)

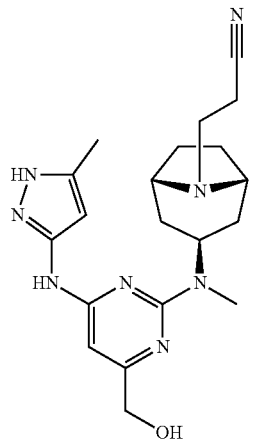 [SMILES: Cc1cc(Nc2cc(CO)nc(N(C)[C@@H]3C[C@H]4CC[C@@H](C3)N4CCC#N)n2)n[nH]1]

(2-(((1R,3s,5S)-8-azabicyclo[3.2.1]octan-3-yl)(methyl)amino)-6-((5-methyl-1H-pyrazol-3-yl)amino)pyrimidin-4-yl)methanol (50 mg, 0.146 mmol) and DIPEA (0.076 ml, 0.437 mmol) were dissolved in MeOH (1.50 ml). Acrylonitrile (0.014 ml, 0.218 mmol) was added and the reaction mixture was stirred at room temperature for 90 min. The reaction mixture was then concentrated in vacuo and the crude residue was purified by preparative reverse phase HPLC (Agilent Dynamax 250×21.4 mm 10 μm, 15 mL/min, 2-60% ACN+0.1% TFA/ACN) to provide the TFA salt of the title compound (14 mg, 19%). (m/z): [M+H]$^+$ calcd for $C_{20}H_{29}N_8O$ 397.25 found 397.1.

Example 1: Crystalline Form I Powder X-Ray Diffraction

The powder X-ray diffraction patterns of FIG. 1 was obtained with a Bruker D8-Advance X-ray diffractometer using Cu-Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The sample was scanned in 20-20 mode from 2° to 35° in 20 with a step size of 0.02° and a scan speed of 0.30° seconds per step. The data acquisition was controlled by Bruker DiffracSuite measurement software and analyzed by Jade software (version 7.5.1). The instrument was calibrated with a corundum standard, within ±0.02° two-theta angle. Observed PXRD peak positions and d-spacings are shown in Table 1 for crystalline Form I.

TABLE 1

| PXRD Data for Crystalline Form I | | | |
|---|---|---|---|
| 2-Theta | d(Å) | Area | A % |
| 5.91 | 14.94 | 10324 | 6.1 |
| 6.28 | 14.06 | 25530 | 15 |
| 6.75 | 13.08 | 27629 | 16.2 |
| 8.08 | 10.94 | 3161 | 1.9 |
| 11.19 | 7.90 | 70185 | 41.3 |
| 11.73 | 7.54 | 170124 | 100 |
| 12.48 | 7.09 | 9018 | 5.3 |
| 13.52 | 6.55 | 12923 | 7.6 |
| 14.25 | 6.21 | 31558 | 18.5 |
| 14.64 | 6.05 | 30799 | 18.1 |
| 15.02 | 5.89 | 5121 | 3 |
| 15.68 | 5.65 | 4744 | 2.8 |
| 16.68 | 5.31 | 9857 | 5.8 |
| 17.62 | 5.03 | 32112 | 18.9 |
| 18.10 | 4.90 | 15613 | 9.2 |
| 18.80 | 4.72 | 109849 | 64.6 |
| 19.29 | 4.60 | 135137 | 79.4 |
| 20.53 | 4.32 | 49854 | 29.3 |
| 21.53 | 4.12 | 2321 | 1.4 |
| 22.16 | 4.01 | 9590 | 5.6 |
| 24.24 | 3.67 | 1915 | 1.1 |
| 25.52 | 3.49 | 8578 | 5 |
| 28.93 | 3.08 | 3263 | 1.9 |
| 29.89 | 2.99 | 10836 | 6.4 |
| 30.44 | 2.93 | 3804 | 2.2 |

Example 2: Analysis of Form I

Figure 2:
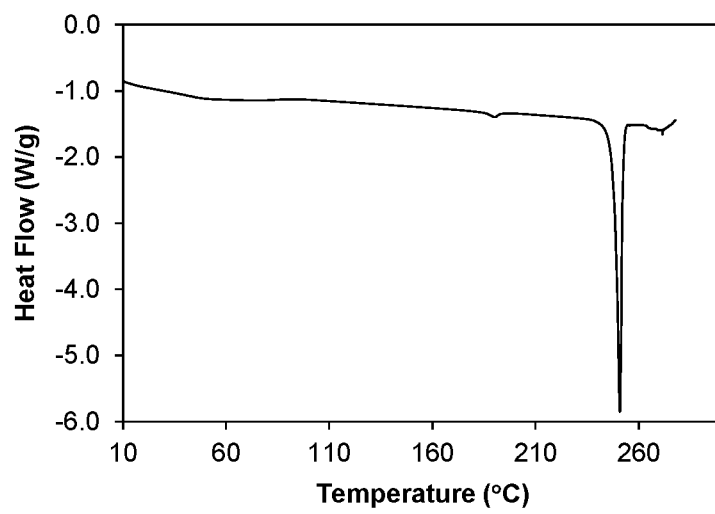
FIG. 2 shows a differential scanning calorimetry (DSC) thermogram of crystalline Form I.

Differential scanning calorimetry (DSC) was performed using a TA Instruments Model Q-100 module with a Thermal Analyst controller. Data were collected and analyzed using TA Instruments Thermal Analysis software. A sample of the crystalline form was accurately weighed into a covered aluminum pan. After a 5 minute isothermal equilibration period at 5° C., the sample was heated using a linear heating ramp of 10° C./min from 0° C. to 300° C. A representative DSC thermogram of the crystalline Form I is shown in FIG. 2. The thermogram shows a melting endotherm with an onset at about 248.5° C., and a peak at about 250.9° C. There were minor pre-melting endothermic thermal events observed at ~40° C. and ~190° C.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 300° C. The balance and furnace chambers were purged with nitrogen flow during use. A representative TGA trace of the crystalline Form I of the invention is shown in FIG. 3. The TGA profile shows a weight loss of about 0.70% between 22° C.-125° C., under $N_2$ purge, and decomposition at an onset temperature of about 250° C.

Figure 4:
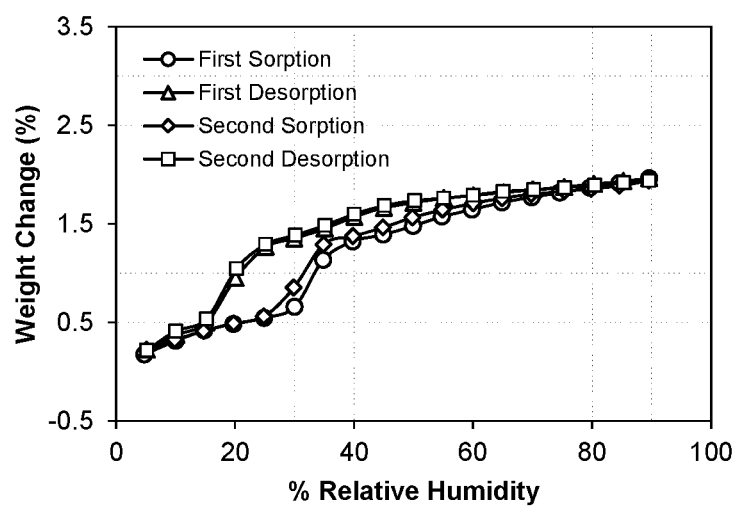
FIG. 4 shows the dynamic moisture sorption isotherm of crystalline Form I.

Dynamic moisture sorption (DMS) measurement was performed using a VTI atmospheric microbalance, SGA-100 system (VTI Corp., Hialeah, Fla. 33016). A weighed sample was used and the humidity was lowest possible value (close to 0% RH) at the start of the analysis. The DMS analysis consisted of an initial drying step (0% RH) for 120 minutes, followed by two cycles of sorption and desorption with a scan rate of 5% RH/step over the humidity range of 5% RH to 90% RH. The DMS run was performed isothermally at 25° C. A representative DMS trace for Form I is shown in FIG. 4. The total moisture uptake between 5 and 90% RH was 1.96%.

Karl Fisher analysis of Form I showed that it contains 1.6% w/w of water.

Preparation 20: Preparation of Form II 28 g of compound 2-6 was suspended in a mixture of 70 mL EtOH and 154 mL THF, then cooled to 5° C. To this suspension was added 82 mL of $LiBH_4$ (2.0M in THF) over 1 hour. After the addition, the temperature was increased to 10° C., and stirred for 2 hours, after which point the starting material was not detected by HPLC analysis. The reaction was then quenched with a mixture of 16.8 g ammonium chloride dissolved in 77 mL water. After heating to 45° C., 467 mL of water was charged over 3 hours. Once 370 mL of this water charge had been added, crystal formation was observed. When the water charge was complete, the slurry was held at 45° C. for 5 hours then ramped to 15° C. over 3 hours. After holding the slurry at 15° C. for 7.5 hours, the product was filtered and rinsed forward with 140 mL EtOH followed by two 140 mL forward rinses using water. The solid was dried under vacuum at 45° C. with a nitrogen bleed overnight to give 22.6 g of Form II (87% yield, 98.6% purity).

21 g of intermediate grade Form II of compound (I), obtained in the previous step, in 63 mL of DMSO was heated to 90° C. 420 mL of n-PrOH were added over 40 minutes while keeping the temperature of the mixture over 86° C. Very fine refractive crystals were observed during the final third of the nPrOH addition. The mixture was stirred for 4 hours at 92° C. The mixture was cooled down to 20° C. over 8 hours and stirred at 20° C. overnight. The product was filtered and washed with 52.5 mL of nPrOH, followed by 52.5 mL of ethanol twice. The solid was dried under vacuum with a nitrogen bleed at 55° C. to give 19.24 g of Form II (92% yield, 99.6% purity).

Example 3: Crystalline Form II Powder X-Ray Diffraction

Figure 5:
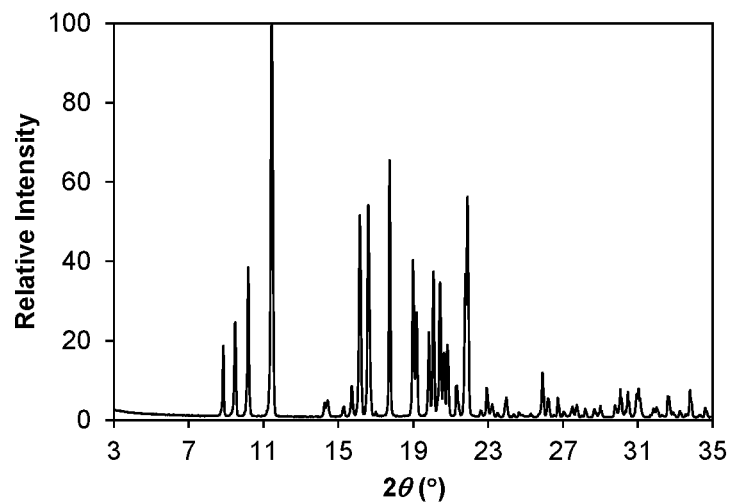
FIG. 5 shows a powder x-ray diffraction (PXRD) pattern of crystalline Form II of compound (I) (hereinafter Form II).

The powder X-ray diffraction patterns of FIG. 5 was obtained under the same conditions as for Form I. Observed PXRD 2θ peak positions and d-spacings are shown in the following Table.

TABLE

PXRD Data for Crystalline Form II

| 2-Theta | d(Å) | Area | A % |
|---|---|---|---|
| 8.9 | 10.0 | 35511 | 9.8 |
| 9.5 | 9.3 | 63058 | 17.4 |
| 10.2 | 8.7 | 91113 | 25.2 |
| 11.4 | 7.7 | 361711 | 100 |
| 14.4 | 6.1 | 29371 | 8.1 |
| 16.2 | 5.5 | 160020 | 44.2 |
| 16.6 | 5.3 | 173568 | 48 |
| 17.7 | 5.0 | 153041 | 42.3 |
| 19.0 | 4.7 | 112788 | 31.2 |
| 19.2 | 4.6 | 93782 | 25.9 |
| 19.8 | 4.5 | 54560 | 15.1 |
| 20.1 | 4.4 | 93452 | 25.8 |
| 20.4 | 4.3 | 111287 | 30.8 |
| 20.6 | 4.3 | 49977 | 13.8 |
| 20.8 | 4.3 | 58656 | 16.2 |
| 21.3 | 4.2 | 27118 | 7.5 |
| 21.9 | 4.1 | 289766 | 80.1 |
| 25.9 | 3.4 | 35768 | 9.9 |
| 30.1 | 3.0 | 26278 | 7.3 |
| 30.5 | 2.9 | 23740 | 6.6 |
| 30.9 | 2.9 | 51901 | 14.3 |
| 32.6 | 2.7 | 22443 | 6.2 |
| 33.8 | 2.7 | 23525 | 6.5 |

Example 4: Analysis of Form II

Form II was tested under conditions similar to Form I.

Figure 6:
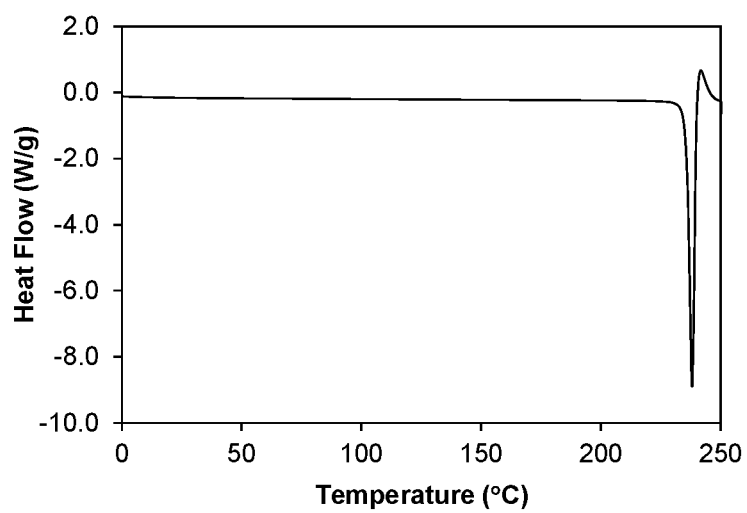
FIG. 6 shows a differential scanning calorimetry (DSC) thermogram of crystalline Form II.

A representative DSC thermogram of the crystalline Form II of the invention is shown in FIG. 6. The thermogram shows a peak in endothermic heat flow, identified as a melt transition, which shows a maximum in endothermic heat flow at a temperature of 238.1° C.±2° C.

A representative TGA trace of the crystalline Form II of the invention is shown in FIG. 7. The TGA profile shows a weight loss associated with decomposition after 222° C.

The DMS analysis consisted of an initial drying step (0% RH) for 120 minutes, followed by two cycles of sorption and desorption with a scan rate of 5% RH/step over the humidity range of 5% RH to 90% RH. The DMS run was performed isothermally at 25° C. A representative DMS trace for Form II is shown in FIG. 8. The total moisture uptake between 5 and 90% RH was about 0.02%.

Example 5: Single Crystal X-Ray Diffraction of Form II

Data were collected on a Rigaku Oxford Diffraction Supernova Dual Source, Cu at Zero, Atlas CCD diffractometer equipped with an Oxford Cryosystems Cobra cooling device. The data were collected using Cu Kα radiation. The structure was solved and refined using the Bruker AXS SHELXTL suite crystallographic software. Full details can be found in the CIF. Unless otherwise stated, hydrogen atoms attached to carbon were placed geometrically and allowed to refine with a riding isotropic displacement parameter. Hydrogen atoms attached to the heteroatoms were located in a difference Fourier map and were allowed to refine freely with an isotropic displacement parameter.

TABLE

Data from Single Crystal X-ray Diffraction Analysis for Form II

| Empirical formula | $C_{20}H_{30}FN_7O_3S$ |
|---|---|
| Formula weight | 467.57 |

TABLE-continued

Data from Single Crystal X-ray Diffraction Analysis for Form II

| | |
|---|---|
| Crystal size | 0.10 × 0.10 × 0.02 mm$^3$ |
| Temperature of Data Collection | 293(2) K |
| Wavelength used for Data Collection | 1.54178 Å |
| Crystal system | Monoclinic |
| Space group | P2$_1$/n |
| Unit cell dimensions | a = 12.4330(8) Å |
| | b = 12.2675(9) Å |
| | c = 14.5337(8) Å |
| | α = 90° |
| | β = 96.996(6)° |
| | γ = 90° |
| Unit cell volume | 2200.2(2) Å$^3$ |
| Z (Number of molecules in the unit cell) | 4 |
| Density (calculated) | 1.412 g/cm$^3$ |
| Theta range for data collection | 4.422 to 75.445° |
| Index ranges | −15 ≤ h ≤ 15 |
| | −12 ≤ k ≤ 15 |
| | −18 ≤ l ≤ 18 |
| Reflections collected | 21349 |
| Independent reflections | 4442 [R(int) = 0.0762] |
| Final R indices [F2 > 2sigma(F2)] | R1 = 0.0568, wR2 = 0.1294 |
| R indices (all data) | R1 = 0.1028, wR2 = 0.1599 |

BIOLOGICAL ASSAYS

Assay 1: Biochemical JAK and Tyk2 Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM MgCl$_2$, and 1 mM EGTA). Recombinant GST-tagged JAK enzymes and a GFP-tagged STAT1 peptide substrate were obtained from Life Technologies.

Serially or discretely diluted compounds were pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and IC$_{50}$ values were determined from a 4-parameter robust fit model with the Prism software (GraphPad Software). Results were expressed as pIC$_{50}$ (negative logarithm of IC$_{50}$) and subsequently converted to pKi (negative logarithm of dissociation constant, Ki) using the Cheng-Prusoff equation.

TABLE 2 pKi values of Compound (I)

| | JAK 1 (pKi) | JAK 2 (pKi) | JAK 3 (pKi) | Tyk 2 (pKi) |
|---|---|---|---|---|
| Compound (I) | 10.2 | 10.2 | 9.1 | 9.9 |

Assay 2: Cellular JAK Potency Assay: Inhibition of IL-13-Induced STAT6 Phosphorylation in BEAS-2B Cells The cellular potency assay for JAK inhibition was carried out by measuring interleukin-13 (IL-13, R&D Systems) induced STAT6 phosphorylation in BEAS-2B human lung epithelial cells (ATCC). The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

BEAS-2B cells were grown at 37° C. in a 5% CO2 humidified incubator in 50% DMEM/50% F-12 medium (Life Technologies) supplemented with 10% FBS (Hyclone), 100 U/mL penicillin, 100 μg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 254 medium, and were allowed to adhere overnight in the incubator. On day 2 of the assay, the medium was removed and replaced with 12 μL of assay buffer (Hank's Balanced Salt Solution/HBSS, 25 mM HEPES, and 1 mg/ml bovine serum albumin/BSA) containing dose-responses of test compounds. The compound was serially diluted in DMSO and then diluted another 1000-fold in media to bring the final DMSO concentration to 0.1%. Cells were incubated with test compounds at 37° C. for 1 h, and followed by the addition of 12 μl of pre-warmed IL-13 (80 ng/mL in assay buffer) for stimulation. After incubating at 37° C. for 30 min, the assay buffer (containing compound and IL-13) was removed, and 10 μL of cell lysis buffer (25 mM HEPES, 0.1% SDS, 1% NP-40, 5 mM MgCl$_2$, 1.3 mM EDTA, 1 mM EGTA, and supplement with Complete Ultra mini protease inhibitors and PhosSTOP from Roche Diagnostics). The plates were shaken at ambient temperature for 30 minutes before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and IC$_{50}$ values were determined from a 4-parameter robust fit model with the Prism software. Results may also be expressed as the negative logarithm of the IC$_{50}$ value, pIC$_{50}$. Compound (I) exhibited a pIC$_{50}$ value of 8.5 in this assay.

Assay 3: Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% CO$_2$ humidified incubator in 50% DMEM/50% F-12 medium (Life Technologies) supplemented with 10% FBS (Hyclone), 100 U/mL penicillin, 100 μg/mL streptomycin (Life Technologies), and 2 mM GlutaMAX (Life Technologies). On day 1 of the assay, cells were seeded at a 500 cells/well density in white 384-well tissue culture plates (Corning) with 25 μL medium, and were allowed to adhere overnight in the incubator. On day 2 of the assay, 5 μL of medium containing dose-responses of test compounds was added, and incubated at 37° C. for 48 h. 30 μL of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as $CC_{15}$. Results were expressed as the negative logarithm of the CC's value, $pCC_{15}$.

It is expected that test compounds exhibiting a lower $pCC_{15}$ value in this assay have less likelihood to cause cytotoxicity. The $pCC_{15}$ for compound (I) was 5.36.

Assay 4: In Vitro TSLP-Induced TARC Assay in Human PBMC

The binding of TSLP to its receptor induces a conformational change that activates JAK1 and JAK2 to phosphorylate various transcription factors including STAT3 and STAT5. In skin-resident immune cells, this triggers a cascade of intracellular events that result in cell proliferation, anti-apoptosis, dendritic cell migration, and production of Th2 cytokines and chemokines. During the acute phase of atopic dermatitis, the skin is invaded by Th2 lymphocytes. In primary peripheral blood mononuclear cells (PBMCs), TSLP has a pro-inflammatory effect by activating myeloid dendritic cells to attract and stimulate T cells. This process is mediated by thymus and activation-regulated chemokine (TARC/CCL17). TARC has proven to be a promising clinical biomarker for atopic dermatitis, with high serum levels indicating accelerated pathogenesis of cutaneous inflammation.

In this assay, it was shown that TSLP stimulation induces TARC release from PBMCs, and that this response is attenuated in a dose-dependent manner upon treatment with compound (I). PBMCs (previously isolated from whole blood and frozen in aliquots at −80° C.) from 3 donors were thawed, plated, and allowed to rest at 37° C. for 1 hour. Cells were pre-treated for 1 hour with a 3.7× dilution series ranging from 33.3 µM to 0.95 nM of compound (I). Cells were then either stimulated with 10 ng/mL TSLP or given an equivalent volume of plain media as a basal control. After 48 hours, the cell supernatants were collected, and TARC was measured using Human CCL17/TARC Quantikine ELISA Kit.

For dose-response analysis, percent inhibition data were plotted vs. compound concentrations, and $IC_{50}$ values were determined from a 4-parameter robust fit model with the GraphPad Prism software. Results may also be expressed as the negative logarithm of the $IC_{50}$ value, $pIC_{50}$. Compound (I) exhibited a $pIC_{50}$ value of 7.8 in this assay.

Assay 5: Rat Pharmacokinetics Assay

The objective of this study was to assess the pharmacokinetics of compound (I) in plasma following single oral (PO, n=3) or intravenous (IV, n=2) administration to male Sprague Dawley rats.

Three male Sprague Dawley rats were administered a single IV dose of compound (I) (1.0 mg/kg in 5% DMSO+20 mM Citrate buffer pH4) via a jugular vein catheter or a single PO dose of 5 mg/kg via oral gavage (5.0 mg/kg in 1% HPMC with 0.1% Tween80). At 0.25, 0.5, 1, 2, 4, 6, and 24 hours after dose administration blood samples were drawn via jugular vein catheter into EDTA tubes and maintained chilled on ice prior to centrifugation (12,000 rpm, 4 min, 4° C.). Aliquots of plasma were transferred to cluster tubes and stored frozen (−80° C.) prior to bioanalysis.

Plasma samples were vortexed prior to transferring a 50 µL aliquot of sample to a 96-well plate and extracted with 200 µL acetonitrile containing an internal standard. Following extraction, samples were centrifuged for 10 min at 3700 RPM (2809×g). The supernatant was transferred to a new 96-well plate and then diluted in 0.2% formic acid in water (3-fold dilution). For all samples, 10 µL was injected onto a Waters Xbridge (C18 30×2.1 mm) column with a flow rate of 0.80 mL/min. Mobile phase A consisted of 0.2% formic acid in water and mobile phase B 0.2% formic acid in acetonitrile. Plasma levels of compound (I) were determined by LC-MS-MS analysis. Standard PK parameters were determined using Phoenix WinNonlin, (Certara Inc.).

TABLE 3

| Pharmacokinetic Parameters | | |
|---|---|---|
| | IV (1 mg/kg) | PO (5 mg/kg) |
| T1/2 (hr) | 1.34 | ND |
| Cmax (µg/ml) | 0.907 | 0.077 |
| AUC (0-t) (µg · hr/ml) | 0.291 | 0.112 |
| CL (L/hr/kg) | 3.54 | ND |
| Vdss (L/Kg) | 1.1 | ND |
| F % | ND | 7.7 |

ND, not determined.

Assay 6: Dermal Pharmacokinetics in Hanford Mini-Pig Skin

The objective of this Study was to determine the epidermal, dermal and plasma pharmacokinetics of compound (I) following a 24 hour exposure to intact Hanford mini-pig skin. Compound (I) was formulated to 0.5 (w/w) in cream or ointment as described, as Formulation A and Formulation B, respectively in Table 4.

TABLE 4

| Formulations of Compound (I) | | | |
|---|---|---|---|
| Formulation A (cream) | | Formulation B (ointment) | |
| Compound (I) | 0.5% | Compound (I) | 0.5% |
| Stearic Acid | 5% | Octylhydroxystearate | 5% |
| Cetostearyl Alcohol | 5% | C8-C10 Triglyceride | 5% |
| Isopropyl Palmitate | 4% | Vaseline (Petrolatum) | 79.5% |
| Octylhydroxystearate | 2% | N-Methylpyrrolidone | 10% |
| BRIJ S2 (PEG 2 Stearyl Ether) | 1.08% | | |
| BRIJ S20 (PEG 20 Stearyl Ether) | 6.92% | | |
| N-Methylpyrrolidine | 10% | | |
| PEG400 | 10% | | |
| RO Water | 55.5% | | |

Twenty-four hours prior to dosing, the hair was shaved from the back of 10-15 kg Hanford mini-pigs exposing an area of at least 700 cm² (about 10% of body surface). At time zero, compound (I) was applied to the back of the mini-pigs at a dose of 25 µL/cm². The skin was covered with an adhesive cover to prevent loss of compound to the cage or bedding. Following 24 h exposure, the backs were gently washed with soap and water to remove non-absorbed drug and patted dry. Immediately following this washing, blood was drawn by venipuncture from the mini-pigs. The outer skin (stratum corneum) was then removed by adhesive tape stripping. Upon exposure of the epidermis a 0.5 cm punch biopsy was taken. The epidermis and dermis were quickly separated, weighed and snap frozen. Similar samples were taken at 94 h, and 168 h (7 days) post-dosing in mini-pigs. Epidermis and dermis samples were homogenized in 1:10 (w/v) water using a Covaris ultrasonic homogenizer. Samples were extracted in 3 volumes of acetonitrile and quantified against a standard curve via LC-MS analysis. As evidenced by the pharmacokinetic parameters (Table 5), significant compound exposure was exhibited in epidermis and dermis layers while the plasma exposure was below the limit of quantitation (0.001 µg/ml) indicating very limited absorption of compound into the systemic circulation.

TABLE 5

Pharmacokinetic Parameters Obtained for Both Formulations of Compound (I)

|  | Formulation A | Formulation B |
| --- | --- | --- |
| Plasma Cmax (µg/ml) | <0.001 | <0.001 |
| Plasma $AUC_{0-t}$ (µg * hr/ml) | <0.001 | <0.001 |
| Epidermis Cmax (µg/g) | 10.9 | 35.8 |
| Epidermis $AUC_{0-t}$ (µg * hr/ml) | 395 | 1320 |
| Dermis Cmax (µg/g) | 0.47 | 1.52 |
| Dermis $AUC_{0-t}$ (µg * hr/ml) | 17.8 | 64.8 |

Assay 7: Ex Vivo JAK Pharmacodynamic (PD) Assay Using Human Freshly Excised Skin An ex vivo JAK pharmacodynamics (PD) assay was conducted using human isolated skin tissue. The PD assay used fresh human skin (dermatome of 750 µm thickness) that was mounted in static Franz cells with a surface area of ~0.5 cm². The receiver chambers of the Franz cells were filled with warm (37° C.) cornification media and placed in an incubator at 37° C. The skin was topically dosed with 10 µL (~18 µL/cm²) of compound (I) or vehicle and was left undisturbed overnight (~24 hours). The next day, with no re-application of the test compound or vehicle, the media was replaced with a Th1-skewed stimulation cocktail consisting of TNFα, IFNγ and IL-12. The skin was left undisturbed for an additional 16 hours, and then harvested and processed for RNA extraction and qPCR of biomarkers: CXCL10, CCL2. GAPDH was used as an internal standard. The compound (I) was formulated in an ointment formulation at 0.5% strength. The composition of the ointment vehicle is listed in Table 6. A total of three skin donors (tested in quadruplicates/sample/treatment) were used. Treatment effect was calculated as the percent increase or decrease in stimulation compared to the vehicle group.

TABLE 6

Composition of Ointment Vehicle

| Octylhydroxystearate | 5% |
| --- | --- |
| C8-C10 Triglyceride | 5% |
| Vaseline (Petrolatum) | 79.5% |
| N-Methylpyrrolidone | 5% |
| Benzyl Alcohol | 5% |

Ex Vivo Human Skin PD Assay Results

The data are summarized in Table 7. CXCL10 gene expression, which encodes interferon-γ-induced protein 10 (IP-10), was inhibited by compound (I) by 90.1% compared to the TH1/vehicle control group. With respect to the CCL2 gene, which encodes monocyte chemoattractant protein 1 (MCP-1), compound (I) inhibited the response by 61.3%. In addition, with both formulations, high concentrations of compound were detected in both the epidermal and dermal layers of the skin.

TABLE 7

Pharmacodynamic effect and epidermal and dermal deposition of 0.5% ointment formulation of compound (I) after about 40 hours of continuous exposure on freshly excised human skin

|  | PD- % Inhibition (mean ± SD) | | PK- Tissue concentration (µM, mean ± SD) | |
| --- | --- | --- | --- | --- |
| Compound (I) | CXCL10 | CCL2 | Epidermis | Dermis |
| 0.5% Ointment | 90.1 ± 15.1 | 61.3 ± 39.6 | 116.5 ± 91.9 | 6.1 ± 5.3 |

Data are presented as mean ± Std dev, n = 12 (3 donors, 4 samples/donor).

Assay 8: Human Skin Permeability Assay

The objective of this experiment was to assess the percutaneous absorption of test compounds through human skin following topical application. The model uses excised human skin mounted in specially designed diffusion chambers (static or flow-through) that allow the skin to be maintained at a temperature and humidity that match real use conditions. The formulation was applied to the surface of the skin and the penetration of the drug is measured by monitoring its rate of appearance in the receptor solution flowing underneath the skin samples. This in vitro system allows carefully control of many of the potential variables involved in topical application, such as dosing volumes, humidity, temperature, drug stability, and skin thickness.

This experiment used a flow-through diffusion cell system (MedFlux-HT™) utilizing a carefully designed flow-path with small void volumes for optimal sink conditions and has been shown to provide local clearance beneath dermatomed skin to generate more accurate and detailed flux profiles through automated collection and optimized fluidics. This system was developed to specifically minimize the dosing area during in vitro experiments, thus allowing more dosing replications within the limited surface area of ex vivo human skin.

The diffusion cells were placed in cell warming supports and heated using a circulating water bath in order to maintain the skin surface temperature at approx. 32° C. The cells were connected to multi-channel peristaltic pumps and maintained at a flow-rate of approximately 10 µL/min (600 µL/hr) for a continuous flow of receiver fluid directly under the skin. Following continuous sampling over 24 h, samples were assayed for test compound levels by LC-MS/MS. The test compound was detected in receiver fluid from 20-28 hours following application of test ointment formulation (n=5). The ointment used is disclosed in Assay 7. The receiver fluid was PBS with 0.1% Brij.

TABLE 8

Flux of compound (I) permeating through 1 cm2 of human skin

|  | MedFlux Permeability (ng/cm2/sec) | | |
| --- | --- | --- | --- |
|  | N | Mean | Std Dev |
| Compound (I) (0.5% Ointment) | 5 | 39.1 | 10.9 |

As shown in Table 8, compound (I) showed adequate permeability.

Assay 9: In Vivo IL-31-pSTAT3 JAK Target Engagement Assay in Mice

An in vivo model of IL-31-induced production of phosphorylated signal transducer and activator of transcription 3 (pSTAT3) in mice was used to assess local target engagement on mouse skin.

The JAK/STAT (janus kinase/signal transducer and activator of transcription) signaling pathway is a key element in the communication between immune cells and is mainly activated through cytokine receptors. Binding of cytokine IL-31 leads to the activation and phosphorylation of JAK1/JAK2 tyrosine kinases which in turn leads to the phosphorylation of STAT3 (pSTAT3). The activated STAT then translocates into the nucleus and directly regulates the transcription of cytokine-sensitive genes. In these studies, Balb/c mice were dosed with an ointment formulation of compound (I). Ointment vehicle (Table 9) or compound (I) formulated in the ointment vehicle was applied topically to shaved skin (25 µl/cm$^2$) 30 minutes before the intradermal injection (50 µl/1×1 cm2 site) of IL-31 (1 µg/ml) at a 1×1 cm$^2$ shaved area of skin on the back between the ears. One hour after IL-31, skin biopsies were collected. The tissue samples were flash frozen and analyzed for pSTAT3 by ELISA and compound concentration. Compound (I) inhibited pSTAT3 production by 80% and the skin tissue concentration of compound (I) was 62 µM.

TABLE 9

Composition of Ointment Vehicle

| | |
|---|---|
| Octylhydroxystearate | 5% |
| C8-C10 Triglyceride | 5% |
| Vaseline (Petrolatum) | 79.5% |
| N-Methylpyrrolidone | 5% |
| Benzyl Alcohol | 5% |

Assay 10: In Vivo TPA-Induced Acute Dermatitis Model in Mice

The objective of this assay is to assess the anti-inflammatory effect of compound (I), in a model of acute dermatitis being studied for cutaneous inflammatory conditions such as atopic dermatitis (Dong et al., *J Pharmacol Exp Ther*, 2013, 344, 436-446).

Topical dermal application of phorbol ester TPA in mice causes an inflammatory response that is characterized by edema and neutrophil influx at the early phase (2-24 h) and by epidermal cell proliferation at the later phase (24-48 h) (Griffiths et al., *Agents and Actions*, 1988, 25, 344-351). In this model, female Balb/c mice were topically administered with 20 µl/ear of either vehicle or TPA (2.5 µg). For the solution formulation, vehicle (1:7 DMSO:Acetone) or test compound was topically applied 30 min before and 15 min after TPA administration. For the ointment formulation, vehicle or compound (I) (0.5% strength) was applied 30 min before TPA. The composition of the ointment vehicle is listed in Table 10. The degree of inflammation was assessed as the change in ear thickness at 6 hours after TPA application.

The results are summarized in Tables 11 and 12. When dosed as a solution, compound (I) (3-1000 µg/ear) inhibited the TPA-induced increase in ear thickness in a dose dependent manner. The highest dose tested inhibited the TPA response by 54.8%. When formulated as an ointment at 0.5% strength, compound (I) inhibited the TPA response by 34.9%.

TABLE 10

Composition of Ointment Vehicle

| | |
|---|---|
| Octylhydroxystearate | 5% |
| C8-C10 Triglyceride | 5% |
| Vaseline (Petrolatum) | 79.5% |
| N-Methylpyrrolidone | 5% |
| Benzyl Alcohol | 5% |

TABLE 11

Effect of topical compound (I) solution formulation on TPA-induced increase in ear thickness in mice

| Compound (I) dose (µg/ear dosed as solution) | Inhibition of TPA-induced increase in ear thickness (mean % inh ± SEM (n)) |
|---|---|
| 30 | 6.6% ± 1.1% (12) |
| 100 | 2.4% ± 0.7% (12) |
| 300 | 35.5% ± 3.1% (12) |
| 1000 | 54.8 ± 2.6% (12) |

TABLE 12

Effect of topical compound (I) ointment formulation on TPA-induced increase in ear thickness in mice

| Compound (I) dose (20 µl/ear) | Inhibition of TPA-induced increase in ear thickness (mean % inh ± SEM (n)) |
|---|---|
| 0.5% Ointment | 34.9% ± 3.3% (12) |

Assay 11: Inhibition of IL-2 Stimulated pSTAT5 in Tall-1 T Cells

The potency of test compounds for inhibition of interleukin-2 (IL-2) stimulated STAT5 phosphorylation was measured in the Tall-1 human T cell line (DSMZ) using AlphaLisa. Because IL-2 signals through JAK1/3, this assay provides a measure of JAK1/3 cellular potency.

Phosphorylated STAT5 was measured via the AlphaLISA SureFire Ultra pSTAT5 (Tyr694/699) kit (PerkinElmer).

Human T cells from the Tall-1 cell line were cultured in a 37° C., 5% $CO_2$ humidified incubator in RPMI (Life Technologies) supplemented with 15% Heat Inactivated Fetal Bovine Serum (FBS, Life Technologies), 2 mM Glutamax (Life Technologies), 25 mM HEPES (Life Technologies) and 1× Pen/Strep (Life Technologies). Compounds were serially diluted in DMSO and dispensed acoustically to empty wells. Assay media (phenol red-free DMEM (Life Technologies) supplemented with 10% FBS (ATCC)) was dispensed (4 µL/well) and plates shaken at 900 rpm for 10 mins. Cells were seeded at 45,000 cells/well in assay media (4 µL/well), and incubated at 37° C., 5% $CO_2$ for 1 hour, followed by the addition of IL-2 (R&D Systems; final concentration 300 ng/mL) in pre-warmed assay media (4 µL) for 30 minutes. After cytokine stimulation, cells were lysed with 6 ul of 3× AlphaLisa Lysis Buffer (PerkinElmer) containing 1× PhosStop and Complete tablets (Roche). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 µL) under green filtered <100 lux light. Plates were shaken at 900 rpm for 2 mins, briefly spun down, and incubated for 2 hrs at RT in the dark. Donor beads were dispensed (5 µL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in a human T cell line. $IC_{50}$ values were determined from analysis of the inhibition curves of signal intensity versus compound concentration. Data are expressed as $pIC_{50}$ (negative decadic logarithm $IC_{50}$) values (mean±standard deviation). Compound (I) exhibited a $pIC_{50}$ value of 8.4 in this assay.

Assay 12: Inhibition of IL-12-Induced STAT4 Phosphorylation in Human CD3+ T Cells This cellular potency assay for JAK inhibition was carried out by measuring interleukin-12 (IL-12, R&D Systems) induced STAT4 phosphorylation in human $CD3^+$ T cells. The CD3 antibody (Becton Dickinson (BD) Biosciences) was conjugated to R-Phycoerythrin (R-PE). The pSTAT4 antibody (pTyr641, BD Biosciences) was conjugated with Alexa Fluor 647.

Human peripheral blood mononuclear cells were cultured at 37° C. in a 5% $CO_2$ humidified incubator in RPMI medium (Life Technologies) supplemented with 10% FBS (Life Technologies), 100 U/mL penicillin, 100 µg/mL streptomycin (Life Technologies), 2 mM GlutaMAX (Life Technologies), plate bound anti CD3 (5 µg/mL, UCHT1, BD Biosciences) and soluble anti-CD28 (1 µg/mL, CD28.2, BD Biosciences) for 3 days. Cells were then resuspended in RPMI medium (Life Technologies) supplemented with 10% FBS (Life Technologies), 100 U/mL penicillin, 100 µg/mL streptomycin (Life Technologies), 2 mM GlutaMAX (Life Technologies) and 10 ng/mL interleukin-2 (IL-2, R&D Systems) for an additional 3 days. On the day of the assay, cells were washed in assay buffer (RPMI supplemented with 0.1% Bovine Serum Albumin (BSA, Sigma), 100 U/mL penicillin, 100 µg/mL streptomycin (Life Technologies) and 2 mM GlutaMAX (Life Technologies)), and resuspended to $1.25 \times 10^6$ cells per mL in assay buffer. Cells were seeded at 250,000 cells per 100 µL per well in a polypropelene, 96 deep well round bottom plate (Corning) and were allowed to culture for 1 hour. The medium was removed and replaced with 50 µL of assay buffer containing dose-responses of test compounds. Compounds were prepared as 10 mM stock solutions in DMSO. Serial dilutions were performed to generate 11 concentrations of test compound at 1000-fold the final assay test concentration in 100% DMSO. These were diluted by 25-fold and then 20-fold into assay media to generate stocks at 2× over the final assay test concentration in 0.2% DMSO. Cells were incubated with test compounds at 37° C. for 1 hour, followed by the addition of 50 µL of pre-warmed assay buffer containing IL-12 (20 ng/mL, R&D Systems) The final concentration of IL-12 is 10 ng/mL. After incubating at 37° C. for 30 minutes, cells were fixed with 100 µL of pre-warmed cytofix buffer (BD Biosciences) and incubated for 10 minutes at 37° C. Cells were then centrifuged for 5 minutes at 322×g, the supernatant discarded and the cells washed with 500 µL of staining buffer (1% BSA in phosphate buffered saline (PBS)). Cells were then centrifuged for 5 minutes at 322×g, the supernatant discarded and the cells were incubated for 30 minutes on ice with 500 µL of pre-chilled Perm III buffer (BD Biosciences) to permeabilize cells. Next, cells were centrifuged for 5 minutes at 322×g, the supernatant discarded, washed with 1 mL of staining buffer, centrifuged once more and the final cell pellet resuspended in 100 µL of staining buffer containing the anti-CD3 R-PE (1:10 dilution) and anti-STAT4 AlexaFluor 647 (1:50 dilution) to stain cell surface and intracellular markers. Cells were incubated for 45 minutes at room temperature in the dark. After antibody staining, cells were centrifuged for 5 minutes at 322×g, the supernatant discarded and the cells were washed with 500 µL of staining buffer. Cells were washed one more time before the well contents were transferred from the deep well assay plate to a polypropylene U-bottomed 96-well plate in 200 µL staining buffer for flow cytometry analysis. For dose-response analysis, mean fluorescence intensity values were plotted vs. compound concentrations, and $IC_{50}$ values were determined from a 4-parameter robust fit model with the Prism software. Compound (I) exhibited a $pIC_{50}$ value of 7.2 in this assay.

Assay 13: Inhibition of IL-13 Stimulated pSTAT6 in Normal Human Epidermal Keratinocytes The potency of test compounds for inhibition of interleukin-13 (IL-13) stimulated STAT6 phosphorylation was measured in the normal human epidermal keratinocytes (ATCC) using AlphaLisa. Phosphorylated STAT6 was measured via the AlphaLISA SureFire Ultra pSTAT6 (Tyr641) kit (PerkinElmer).

Primary epidermal keratinocytes were cultured in a 37° C., 5% $CO_2$ humidified incubator in dermal cell basal medium (ATCC) supplemented with keratinocyte growth kit (ATCC) and 1× Pen/Strep (Life Technologies). Cells were seeded at 20,000 cells/well in white poly-D-lysine-coated 384-well plates (Corning) with 50 µl and incubated at 37° C., 5% $CO_2$ for overnight. On day 2 of the assay, the medium was removed and replaced with 154 of medium containing does-response of test compounds. Compounds were serially diluted in DMSO and then diluted another 1000-fold in media to bring the final DMSO concentration to 0.1%. Cells were incubated with test compounds at 37° C. for 1 h, and followed by the addition of followed by the addition of IL-13 (R&D Systems; final concentration 50 ng/mL) in pre-warmed assay media (5 µL) for 30 minutes.

After cytokine stimulation, cells were lysed with 5 ul of 5× AlphaLisa Lysis Buffer (PerkinElmer) containing 1× PhosStop and Complete tablets (Roche). The lysate was shaken at 900 rpm for 10 minutes at room temperature (RT). Phosphorylated STAT6 was measured via the pSTAT6 AlphaLisa kit (PerkinElmer). Freshly prepared acceptor bead mixture was dispensed onto lysate (10 µL) under green filtered <100 lux light. Plates were shaken at 900 rpm for 2 mins, briefly spun down, and incubated for 2 hrs at RT in the dark. Donor beads were dispensed (10 µL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

Luminescence signals were recorded and utilized to calculate the percent inhibition values based on DMSO and controls. For dose-response analysis, percent inhibition data were plotted vs. compound concentrations, and $IC_{50}$ values were determined from a 4-parameter robust fit model with the Prism software. The $pIC_{50}$ of compound (I) was 8.3 in this assay.

Assay 14: Inhibition of IL-22 Stimulated pSTAT3 in Normal Human Epidermal Keratinocytes The potency of test compounds for inhibition of interleukin-22 (IL-22) stimulated STAT3 phosphorylation was measured in the normal human epidermal keratinocytes (ATCC) using AlphaLisa. Phosphorylated STAT3 was measured via the AlphaLISA SureFire Ultra pSTAT3 (Tyr705) kit (PerkinElmer).

Primary epidermal keratinocytes were cultured in a 37° C., 5% $CO_2$ humidified incubator in dermal cell basal medium (ATCC) supplemented with keratinocyte growth kit (ATCC) and 1× Pen/Strep (Life Technologies). Cells were seeded at 20,000 cells/well in white poly-D-lysine-coated 384-well plates (Corning) with 50 µl and incubated at 37° C., 5% $CO_2$ for overnight. On day 2 of the assay, the medium was removed and replaced with 154 of medium containing dose-response of test compounds. Compounds were serially diluted in DMSO and then diluted another 1000-fold in media to bring the final DMSO concentration to 0.1%. Cells were incubated with test compounds at 37° C. for 1 h, and followed by the addition of followed by the addition of IL-22 (R&D Systems; final concentration 50 ng/mL) in pre-warmed assay media (5 µL) for 30 minutes.

After cytokine stimulation, cells were lysed with 5 ul of 5× AlphaLisa Lysis Buffer (PerkinElmer) containing 1× PhosStop and Complete tablets (Roche). The lysate was shaken at 900 rpm for 10 minutes at room temperature (RT). Phosphorylated STAT3 was measured via the pSTAT3 AlphaLisa kit (PerkinElmer). Freshly prepared acceptor bead mixture was dispensed onto lysate (10 µL) under green filtered <100 lux light. Plates were shaken at 900 rpm for 2 mins, briefly spun down, and incubated for 2 hrs at RT in the dark. Donor beads were dispensed (10 µL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

Luminescence signals were recorded and utilized to calculate the percent inhibition values based on DMSO and controls. For dose-response analysis, percent inhibition data were plotted vs. compound concentrations, and $IC_{50}$ values were determined from a 4-parameter robust fit model with the Prism software. The $pIC_{50}$ of compound (I) was 8.4 in this assay.

Assay 15: Recovery of IL-22 Suppressed Filaggrin in Normal Human Epidermal Keratinocytes IL-22 is known to inhibit the expression of terminal differentiation genes, such as Filaggrin. The recovery level of test compound for interleukin-22 (IL-22) suppressed Filaggrin expression was measured in the normal human epidermal keratinocytes (ATCC) using real-time PCR.

Primary epidermal keratinocytes were cultured in a 37° C., 5% $CO_2$ humidified incubator in dermal cell basal medium (ATCC) supplemented with keratinocyte growth kit (ATCC) and 1× Pen/Strep (Life Technologies). Cells were seeded at 5,000 cells/well in BioCoat 96-well plates (Corning) with 100 µl and incubated at 37° C., 5% $CO_2$ for 3 to 4 days till 100% confluency. Then, the medium was removed and replaced with 150 µL of medium containing does-response of test compounds. Compounds were serially diluted in DMSO and then diluted another 1000-fold in media to bring the final DMSO concentration to 0.1%. On day 1 of the assay, cells were incubated with test compounds at 37° C. for 1 h, and followed by the addition of followed by the addition of IL-22 (R&D Systems; final concentration 50 ng/mL) in pre-warmed media (50 µL) for 4 days. The medium with test compounds and IL-22 was changed once on day 3. On day 5, cells were washed with 1×PBS (Gibco) and lysed with 50 µl of Lysis Buffer containing 0.5 µl DnaseI from TaqMan® Gene Expression Cells-to-Ct™ Kit (Life Technologies). After incubation at room temperature (RT) for 5 minutes, 5 µl of Stop solution from the kit was added and then incubated at RT for 2 minutes. 11.25 µl of lysate, 12.5 µl of 2× RT buffer and 1.25 µl 20× RT enzyme mix from the kit were mixed. The reverse transcription reaction was carried out by incubating the mixture at 37° C. for 60 minutes and then 95° C. for 5 minutes to generate cDNA. To assemble the PCR cocktail, each reaction contained 10 µl of 2× TaqMan® Gene Expression Mater Mix, 1 µl of 2× TagMan® Filaggrin Gene Expression Assay (Life Technologies), 1 µl of 2× TaqMan® UBC Gene Expression Assay (Life Technologies), 4 µl of nuclease-free water and 4 µl of cDNA. PCR reactions were done on StepOnePlus™ (Life Technologies) with cycling conditions of 50° C. for 2 minutes, 95° C. for 10 minutes followed by 40 cycles of 95° C. for 15 seconds and 60° C. for 1 minute. Fluorescence signals were captured after each cycle. Comparative $C_T$ method was used to quantify gene expression with cells without IL-22 and test compounds as baseline control.

The recovery of compound (I) for interleukin-22 (IL-22) suppressed Filaggrin expression was observed at a concentration <1 µM.

Assay 16: Caco-2 Permeation Assay

The Caco-2 permeation assay was used as an indication of skin permeability. The assay measures the rate at which test compounds in solution permeate a cell monolayer (designed to mimic the tight junction of human small intestinal monolayers).

CacoReady 24-well transwell plates were obtained from ADMEcell (Alameda, Calif.). The compounds were evaluated at a concentration of 5 µM from 10 mM DMSO stock solutions in duplicate (n=2). The passive permeability of the compounds tested was evaluated using Caco-2 cell monolayers along with Verapamil (25 µM) to inhibit P-gp transport proteins in the apical to basolateral (A-B) direction. The experiment was conducted in a 37° C., 5% $CO_2$ incubator. Caco-2 culture media consisted of standard filtered DMEM, FCS 10%, L-Glutamine 1% and PenStrep 1%. Basal assay plate was prepared by adding 750 µL of transport buffer to A-B wells. A CacoReady™ plate was prepared by removing the Caco-2 media from the apical wells and replacing with fresh transport media (200 µL repeated for a total of 3 washes). Blank media (200 µL) was then replaced with diluted compound for A-B wells. To begin the incubation, the basal plate was removed from the incubator and the apical section was added on top of it. Samples (40 µL) were collected from the apical and basal compartments for time zero (t0). Samples were collected again after 120 minutes (t120) from the apical and basal compartments. All samples were diluted and prepared for bioanalysis by LC-MS/MS. The permeation coefficient ($K_p$, mean A to B+Verapamil Papparent) in cm/sec was calculated as dQ (flux)/(dt×Area× concentration).

In this assay, a compound with a $K_r$ value of less than about $5 \times 10^{-6}$ cm/sec is considered to have low permeability. A compound having a $K_r$ value of more than about $20 \times 10^{-6}$ cm/sec is considered to have high permeability.

Assay 17: Human Liver Microsome Assay

The objective of this assay was to assess the metabolic stability of test compounds in an in vitro human liver sub-fraction. Human liver microsomes obtained from Bioreclamation-IVT (Baltimore, Md.) were thawed on ice and diluted into 0.1M potassium phosphate buffer pH 7.4 to yield final incubation protein concentrations of 0.1 mg/mL. Test compounds (10 mM) were diluted into NADPH cofactor to yield final incubation concentrations of 0.1 µM test compound and 1 mM NADPH. Incubations were conducted at 37° C. temperature and test aliquots were taken at time points 0, 5, 8, 15, 30 and 45 minutes. Each aliquot was crashed into water with 3% formic acid and 1 µM internal standard. The resulting samples were injected onto an LC-MS/MS system for analysis.

For each incubation, the peak area of the analytes in each t0 aliquot was set to 100% and the peak areas from subsequent time point aliquots were converted to percentage of parent compound remaining relative to t0. The percentage of parent compound remaining was converted to natural log scale and plotted versus time in minutes. A linear regression analysis was performed for the initial decline of the parent disappearance profile and a formula for the best-fit line determined. The slope of the resultant line was normalized to protein concentration in mg/mL protein or number of cells/mL and $CL_{int}$ was calculated as follows for liver microsomes:

$$CL_{int}(\mu L \cdot min^{-1} \cdot mg^{-1}) = (Slope \times 1000)/[protein, mg/mL]$$

$CL_{int}$ values from 0-8 μl/min/mg represent low clearance (i.e <30% of hepatic blood flow in human). $CL_{int}$ values from 9-49 μl/min/mg represent moderate clearance (i.e. 30-70% of hepatic blood flow in human) and values >50 μl/min/mg represent high hepatic clearance (i.e. >70% of hepatic blood flow in human).

Characterization of Compound (I) and Comparison Compounds

TABLE 13

Characterization of comparison compounds

| Compound # | Structure | $Caco_{verap}$ $K_p$ $10^{-6}$ cm/sec | HLM $CI_{int}$ μL/min/mg |
|---|---|---|---|
| (I) | 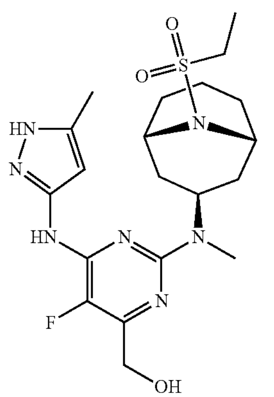 [SMILES: CCS(=O)(=O)N1[C@@H]2CCC[C@H]1C[C@H](N(C)c1nc(CO)c(F)c(Nc3cc(C)[nH]n3)n1)C2] | 42.3 | 136 |
| C-1 | 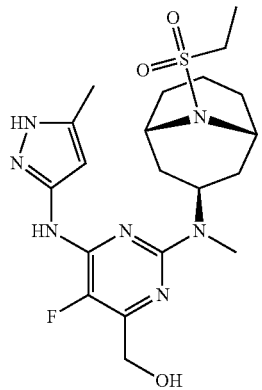 | 3.55 | 6 |
| C-2 | 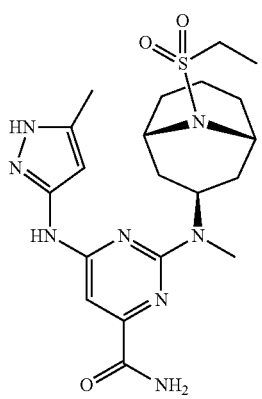 [SMILES: CCS(=O)(=O)N1[C@@H]2CCC[C@H]1C[C@H](N(C)c1nc(Nc3cc(C)[nH]n3)cc(C(N)=O)n1)C2] | 5.5 | 12 |

TABLE 13-continued

Characterization of comparison compounds

Comparative compounds C-1 and C-2 were disclosed by applicant in some presentations made in April, June and August 2017 at conferences.

Compound (I) is characterized by a much higher permeability ($Caco_{verap}$ value) and human liver microsome clearance (HLM $CI_{int}$ value) than C-1 and C-2. A higher clearance is beneficial to promote quick systemic clearance and prevent systemic exposure which may be associated with side effects. Higher permeability is beneficial for skin indications as it seems to provide for better penetration in the skin.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A method of inhibiting JAK enzymes in a patient in need thereof comprising administering to the patient a compound of formula (I):

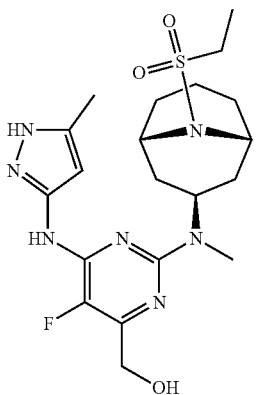 (I)

or a pharmaceutically-acceptable salt thereof.

2. The method of claim 1, wherein the JAK enzymes are JAK1, JAK2, JAK3 and TYK2.

3. The method of claim 1, wherein compound of formula (I) is administered as a free base form.

4. The method of claim 1, wherein compound of formula (I) is administered as a pharmaceutically-acceptable salt thereof.

5. The method of claim 1, wherein the compound of formula (I), or a pharmaceutically-acceptable salt thereof, is administered to the skin of the patient.

6. The method of claim 5, wherein the compound of formula (I), or a pharmaceutically-acceptable salt thereof, is administered in a pharmaceutical composition.

7. The method of claim 6, wherein the pharmaceutical composition is an ointment.

8. The method of claim 6, wherein the pharmaceutical composition is a cream.

9. The method of claim 6, wherein the pharmaceutical composition is a lotion, a gel, a stick, a spray, a paste, a foam, or a mousse.

10. The method of claim 6, wherein the pharmaceutical composition comprises between 0.1 and 10% by weight of compound of formula (I), or a pharmaceutically acceptable salt thereof.

11. The method of claim 6, wherein the pharmaceutical composition comprises between 0.25 and 5% by weight of compound of formula (I), or a pharmaceutically acceptable salt thereof.

12. The method of claim 6, wherein the pharmaceutical composition comprises between 0.05 and 0.5% by weight of compound of formula (I), or a pharmaceutically acceptable salt thereof.

13. The method of claim 1, wherein the patient suffers from an inflammatory disease.

14. The method of claim 1, wherein the patient suffers from an inflammatory skin disease.

15. The method of claim 14, wherein the inflammatory skin disease is atopic dermatitis.

16. The method of claim 1, wherein the patient suffers from an autoimmune skin disease.

17. The method of claim 16, wherein the autoimmune skin disease is alopecia areata.

18. The method of claim 1, wherein the patient suffers from an inflammatory or autoimmune skin disease selected from the group consisting of: vitiligo, prurigo nodularis, lichen planus, contact dermatitis, skin manifestations of graft versus host disease, pemphigoid, discoid lupus, lichen sclerosus, lichen planopilaris, psoriasis, and foliculitis decalvans.

* * * * *